(12) United States Patent
Sakai, Jr. et al.

(10) Patent No.: US 8,517,932 B2
(45) Date of Patent: Aug. 27, 2013

(54) METHODS AND DEVICES FOR PROVIDING ACCESS THROUGH TISSUE TO A SURGICAL SITE

(75) Inventors: Kiyoto Benjamin Sakai, Jr., Cincinnati, OH (US); Shailendra K. Parihar, Mason, OH (US); Mark S. Zeiner, Mason, OH (US); Edgar V. Menezes, Jacksonville, FL (US); Aron O. Zingman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 788 days.

(21) Appl. No.: 12/636,191

(22) Filed: Dec. 11, 2009

(65) Prior Publication Data

US 2011/0144444 A1    Jun. 16, 2011

(51) Int. Cl.
*A61B 1/32* (2006.01)

(52) U.S. Cl.
USPC ........................................................ 600/206

(58) Field of Classification Search
USPC ................................ 600/188–199, 201–210
See application file for complete search history.

(56) References Cited

U.S. PATENT DOCUMENTS

| | | | |
|---|---|---|---|
| 3,397,699 A | 8/1968 | Kohl |
| 4,022,191 A | 5/1977 | Jamshidi |
| 4,608,977 A | 9/1986 | Brown |
| 4,809,694 A | 3/1989 | Ferrara |
| 5,031,634 A | 7/1991 | Simon |
| 5,053,042 A | 10/1991 | Bidwell |
| 5,100,387 A | 3/1992 | Ng |
| 5,122,122 A | 6/1992 | Allgood |
| 5,201,742 A | 4/1993 | Hasson |
| 5,232,451 A | 8/1993 | Freitas et al. |
| 5,235,987 A | 8/1993 | Wolfe |
| 5,312,417 A | 5/1994 | Wilk |
| 5,316,014 A | 5/1994 | Livingston |
| 5,320,111 A | 6/1994 | Livingston |
| 5,330,437 A | 7/1994 | Durman |
| 5,330,497 A | 7/1994 | Freitas et al. |

(Continued)

FOREIGN PATENT DOCUMENTS

| | | |
|---|---|---|
| EP | 577400 A1 | 1/1994 |
| EP | 2119405 | 11/2009 |

(Continued)

OTHER PUBLICATIONS

U.S. Appl. No. 12/339,473, filed Mar. 6, 2009, Methods and Devices for Providing Access Into a Body Cavity.

(Continued)

*Primary Examiner* — Eduardo C Robert
*Assistant Examiner* — Tara Carter
(74) *Attorney, Agent, or Firm* — Nutter McClennen & Fish LLP

(57) ABSTRACT

Methods and devices are provided for providing surgical access into a body cavity. A surgical access port is provided that has an adjustable longitudinal length, such as by being formed from multiple segments configured to move relative to one another. An anchor can be coupled to a distal end of the surgical access port to help secure the surgical access port within a tissue opening by engaging a distal side of the tissue. Optionally, the anchor can be removably coupled to the distal end of the surgical access port, thereby allowing any one of a plurality of anchors to be selectively coupled thereto.

19 Claims, 16 Drawing Sheets

(56) References Cited

U.S. PATENT DOCUMENTS

| | | | |
|---|---|---|---|
| 5,342,315 A | 8/1994 | Rowe et al. | |
| 5,431,676 A | 7/1995 | Dubrul et al. | |
| 5,468,248 A | 11/1995 | Chin et al. | |
| 5,494,039 A | 2/1996 | Onik et al. | |
| 5,569,205 A | 10/1996 | Hart et al. | |
| 5,618,309 A | 4/1997 | Green et al. | |
| 5,628,732 A | 5/1997 | Antoon, Jr. et al. | |
| 5,647,373 A | 7/1997 | Paltieli et al. | |
| 5,697,946 A | 12/1997 | Hopper et al. | |
| 5,707,359 A | 1/1998 | Bufalini | |
| 5,738,628 A | 4/1998 | Sierocuk et al. | |
| 5,755,697 A | 5/1998 | Jones et al. | |
| 5,782,800 A * | 7/1998 | Yoon | 604/514 |
| 5,836,913 A | 11/1998 | Orth et al. | |
| 5,857,999 A | 1/1999 | Quick et al. | |
| 5,868,673 A | 2/1999 | Vesely | |
| 5,882,340 A | 3/1999 | Yoon | |
| 5,911,707 A | 6/1999 | Wolvek et al. | |
| 5,916,147 A | 6/1999 | Boury | |
| 5,916,175 A | 6/1999 | Bauer et al. | |
| 5,941,889 A | 8/1999 | Cermak | |
| 5,954,670 A | 9/1999 | Baker | |
| 5,984,930 A | 11/1999 | Maciunas et al. | |
| 6,017,356 A | 1/2000 | Frederick et al. | |
| 6,030,365 A | 2/2000 | Laufer | |
| D422,706 S | 4/2000 | Bucholz et al. | |
| 6,048,321 A | 4/2000 | McPherson et al. | |
| 6,110,182 A | 8/2000 | Mowlai-Ashtiani | |
| 6,162,196 A | 12/2000 | Hart et al. | |
| 6,195,577 B1 | 2/2001 | Truwit et al. | |
| 6,203,499 B1 | 3/2001 | Imling | |
| 6,216,029 B1 | 4/2001 | Paltieli et al. | |
| 6,231,565 B1 | 5/2001 | Tovey et al. | |
| 6,231,585 B1 | 5/2001 | Takahashi et al. | |
| 6,236,875 B1 | 5/2001 | Bucholz et al. | |
| 6,245,028 B1 | 6/2001 | Furst et al. | |
| 6,254,571 B1 * | 7/2001 | Hart | 604/107 |
| 6,283,942 B1 | 9/2001 | Staehlin et al. | |
| 6,361,499 B1 | 3/2002 | Bates et al. | |
| 6,379,307 B1 | 4/2002 | Filly et al. | |
| 6,400,979 B1 | 6/2002 | Stoianovici et al. | |
| 6,443,960 B1 | 9/2002 | Brabrand et al. | |
| 6,445,943 B1 | 9/2002 | Ferre et al. | |
| 6,451,042 B1 | 9/2002 | Bonutti | |
| 6,468,226 B1 | 10/2002 | McIntyre, IV | |
| 6,475,152 B1 | 11/2002 | Kelly, Jr. et al. | |
| 6,490,467 B1 | 12/2002 | Bucholz et al. | |
| 6,501,981 B1 | 12/2002 | Schweikard et al. | |
| 6,529,765 B1 | 3/2003 | Franck et al. | |
| 6,535,756 B1 | 3/2003 | Simon et al. | |
| 6,539,121 B1 | 3/2003 | Haskell et al. | |
| 6,546,279 B1 | 4/2003 | Bova et al. | |
| 6,547,782 B1 | 4/2003 | Taylor | |
| 6,551,270 B1 | 4/2003 | Bimbo et al. | |
| 6,582,439 B1 | 6/2003 | Sproul | |
| 6,665,554 B1 | 12/2003 | Charles et al. | |
| 6,687,531 B1 | 2/2004 | Ferre et al. | |
| 6,723,106 B1 | 4/2004 | Charles et al. | |
| 6,731,966 B1 | 5/2004 | Spigelman et al. | |
| 6,752,812 B1 | 6/2004 | Truwit | |
| 6,770,027 B2 | 8/2004 | Banik et al. | |
| 6,782,288 B2 | 8/2004 | Truwit | |
| 6,783,524 B2 | 8/2004 | Anderson | |
| 6,785,572 B2 | 8/2004 | Yanof et al. | |
| 6,808,492 B2 | 10/2004 | Snyder | |
| 7,021,173 B2 | 4/2006 | Stoianovici et al. | |
| 7,056,329 B2 | 6/2006 | Kerr | |
| 7,076,106 B2 | 7/2006 | Haskell et al. | |
| 7,083,626 B2 | 8/2006 | Hart et al. | |
| 7,163,525 B2 | 1/2007 | Franer | |
| 7,371,227 B2 | 5/2008 | Zeiner | |
| 7,905,907 B2 | 3/2011 | Spitler et al. | |
| 8,206,417 B2 | 6/2012 | Maahs et al. | |
| 2003/0100814 A1 | 5/2003 | Kindlein | |
| 2003/0208207 A1 | 11/2003 | Layer | |
| 2003/0229338 A1 | 12/2003 | Irion et al. | |
| 2004/0082969 A1 | 4/2004 | Kerr | |
| 2004/0185453 A1 | 9/2004 | Myerson et al. | |
| 2004/0230161 A1 | 11/2004 | Zeiner | |
| 2004/0254426 A1 | 12/2004 | Wenchell | |
| 2005/0119685 A1 | 6/2005 | Smith | |
| 2005/0222582 A1 * | 10/2005 | Wenchell | 606/108 |
| 2006/0069414 A1 | 3/2006 | Imran et al. | |
| 2006/0149137 A1 | 7/2006 | Pingleton et al. | |
| 2006/0247499 A1 | 11/2006 | Butler et al. | |
| 2006/0247673 A1 | 11/2006 | Voegele et al. | |
| 2007/0175929 A1 | 8/2007 | Schram | |
| 2007/0185453 A1 | 8/2007 | Michael et al. | |
| 2007/0260121 A1 | 11/2007 | Bakos et al. | |
| 2007/0260273 A1 | 11/2007 | Cropper et al. | |
| 2008/0086080 A1 | 4/2008 | Mastri et al. | |
| 2008/0086167 A1 | 4/2008 | Mastri et al. | |
| 2008/0249373 A1 | 10/2008 | Wenchell | |
| 2008/0255519 A1 | 10/2008 | Piskun et al. | |
| 2009/0005799 A1 | 1/2009 | Franer et al. | |
| 2009/0105659 A1 | 4/2009 | Bettuchi et al. | |
| 2009/0306586 A1 | 12/2009 | Ross et al. | |
| 2010/0081863 A1 | 4/2010 | Hess et al. | |
| 2010/0081864 A1 | 4/2010 | Hess et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2011/0023987 A1 | 2/2011 | Zucker et al. | |

FOREIGN PATENT DOCUMENTS

| | | |
|---|---|---|
| WO | 9636283 A1 | 11/1996 |
| WO | 0041759 A1 | 7/2000 |
| WO | 0062689 A1 | 10/2000 |
| WO | 0108563 A2 | 2/2001 |
| WO | WO-2005037079 A2 | 4/2005 |
| WO | 2005097019 A2 | 10/2005 |
| WO | 2005097234 A2 | 10/2005 |
| WO | 2006057982 A2 | 6/2006 |

OTHER PUBLICATIONS

U.S. Appl. No. 12/399,482, filed Mar. 6, 2009, Methods and Devices for Providing Access Into a Body Cavity.

U.S. Appl. No. 12/399,547, filed Mar. 6, 2009, Surgical Access Devices and Methods Providing Seal Movement in Predefined Paths.

U.S. Appl. No. 12/399,625, filed Mar. 6, 2009, Methods and Devices for Providing Access Into a Body Cavity.

U.S. Appl. No. 12/420,146, filed Apr. 8, 2009, Methods and Devices for Providing Access Into a Body Cavity.

U.S. Appl. No. 12/424,213, filed Apr. 15, 2009, Cannula With Sealing Elements.

U.S. Appl. No. 12/478,862, filed Jun. 5, 2009, Flexible Cannula Devices and Methods.

U.S. Appl. No. 12/478,882, filed Jun. 5, 2009, Multi-Planar Obturator With Foldable Retractor.

U.S. Appl. No. 12/479,030, filed Jun. 5, 2009, Retractor With Integrated Wound Closure.

U.S. Appl. No. 12/479,096, filed Jun. 5, 2009, Interlocking Seal Components.

U.S. Appl. No. 12/479,293, filed Jun. 5, 2009, Methods and Devices for Providing Access Through Tissue to Surgical Site.

U.S. Appl. No. 12/479,395, filed Jun. 5, 2009, Methods and Devices for Accessing a Body Cavity Using Surgical Access Device With Modular Seal Components.

U.S. Appl. No. 12/512,542, filed Jul. 30, 2009, Methods and Devices for Providing Access Into a Body Cavity.

U.S. Appl. No. 12/512,568, filed Jun. 30, 2009, Methods and Devices for Providing Access Into a Body Cavity.

U.S. Appl. No. 12/636,205, filed Dec. 11, 2009, Methods and Devices for Providing Access Through Tissue to a Surgical Site.

U.S. Appl. No. 12/636,232, filed Dec. 11, 2009, Methods and Devices for Providing Access Through Tissue to a Surgical Site.

U.S. Appl. No. 12/636,020, filed Dec. 11, 2009, Inverted Conical Expandable Retractor.

U.S. Appl. No. 12/636,023, filed Dec. 11, 2009, Inverted Concical Expandable Retractor With Coil Spring.
U.S. Appl. No. 12/635,754, filed Dec. 11, 2009, Methods and Devices for Providing Access Into a Body Cavity.
U.S. Appl. No. 12/635,762, filed Dec. 11, 2009, Methods and Devices for Providing Access Into a Body Cavity.
U.S. Appl. No. 12/635,990, filed Dec. 11, 2009, Methods and Devices for Accessing a Body Cavity.

U.S. Appl. No. 12/623,018, filed Nov. 20, 2009, Discrete Flexion Head for Single Port Device.
International Search Report and Written Opinion for International App. No. PCT/US2010/059617 dated Mar. 29, 2011.
U.S. Appl. No. 12/636,184, filed Dec. 11, 2009.
U.S. Appl. No. 12/636,174, filed Dec. 11, 2009.

* cited by examiner

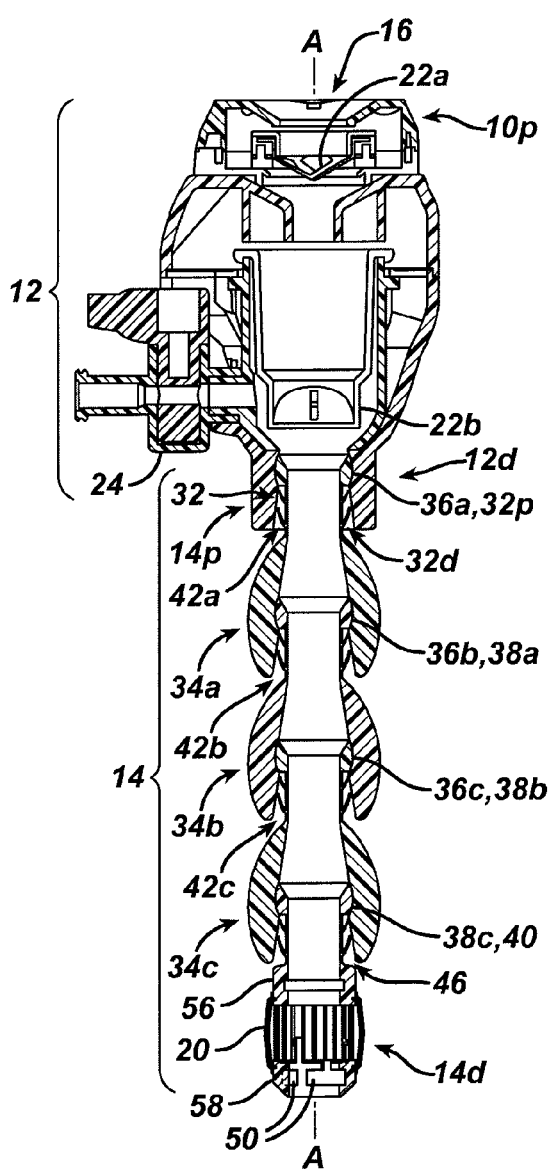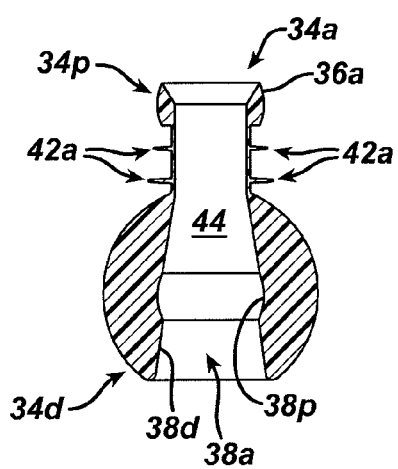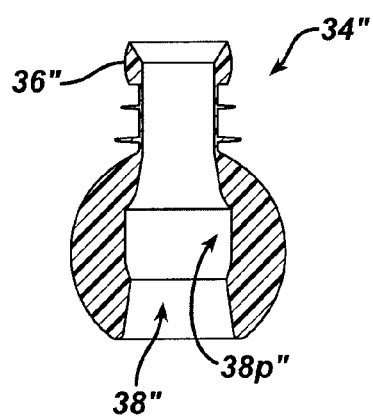

FIG. 7
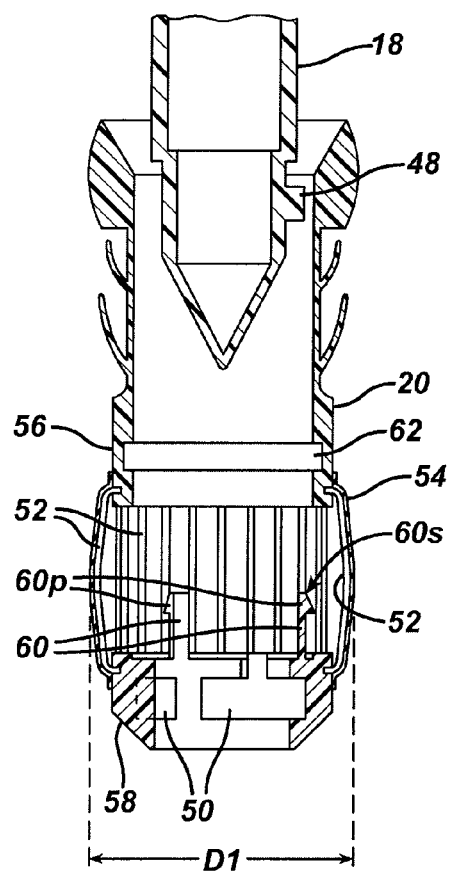
FIG. 8
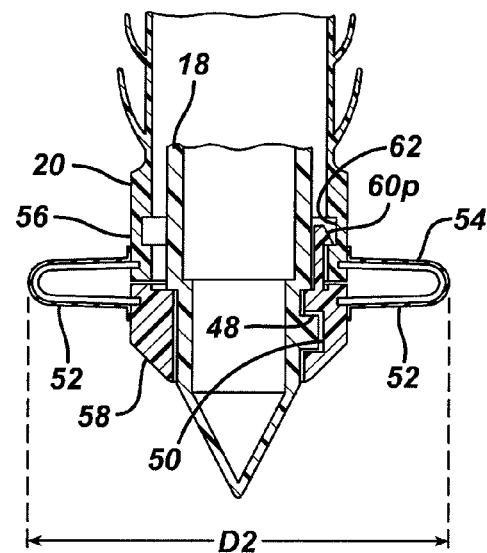
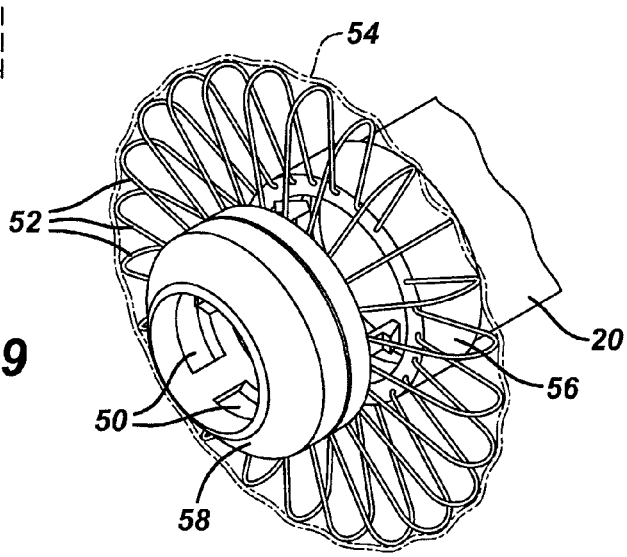
FIG. 9

FIG. 27
FIG. 28
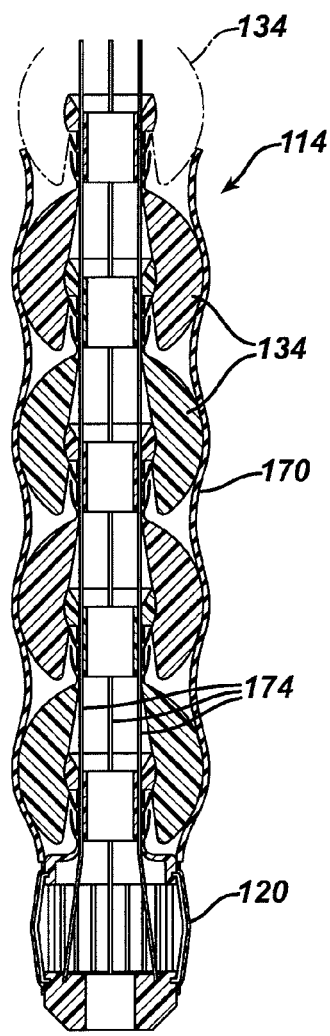
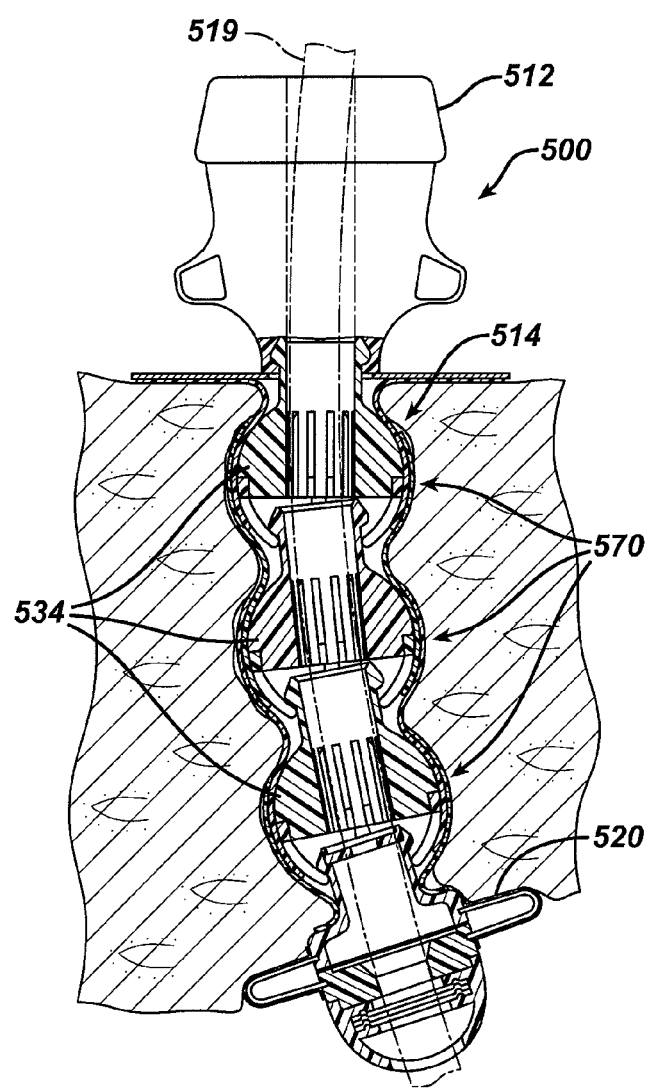

FIG. 36
FIG. 37
FIG. 38
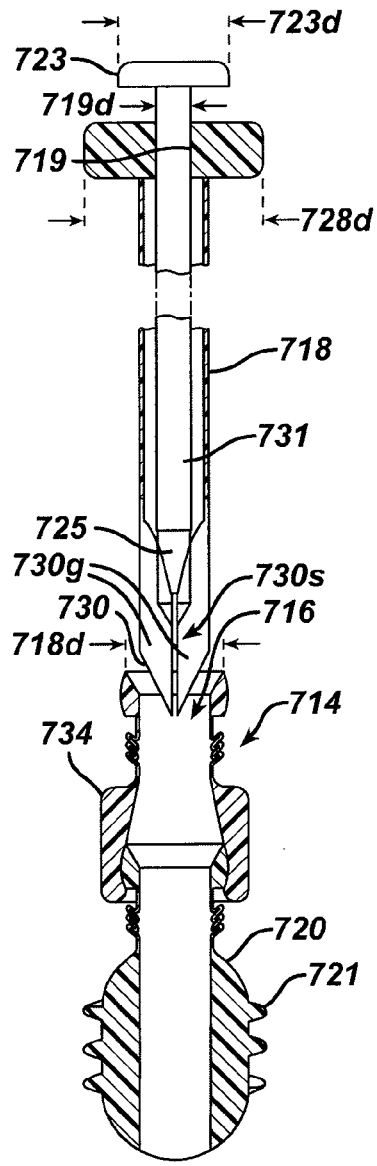
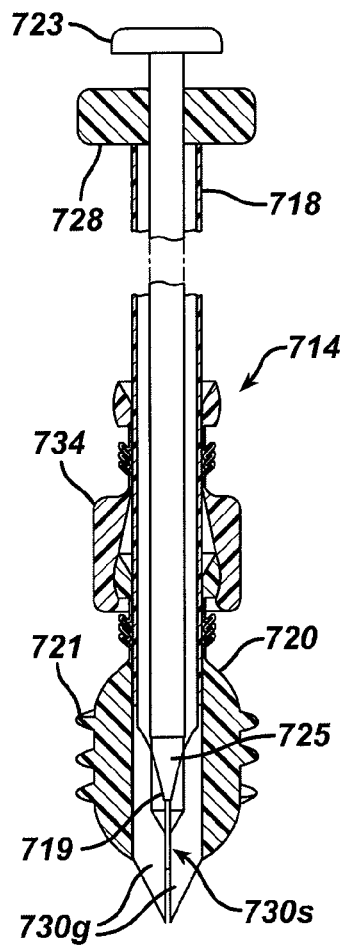
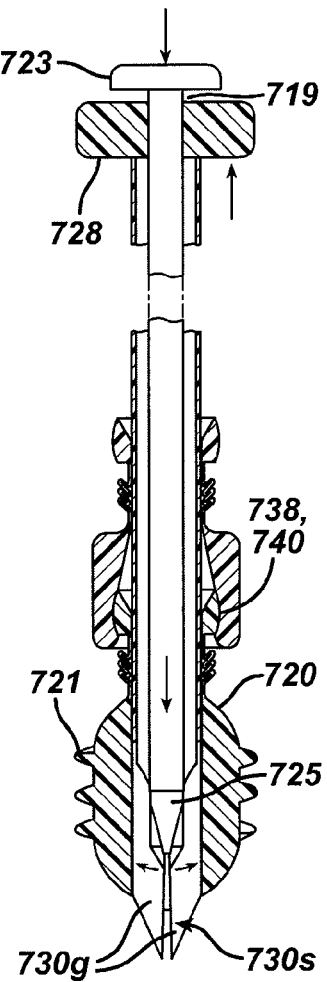

METHODS AND DEVICES FOR PROVIDING ACCESS THROUGH TISSUE TO A SURGICAL SITE

CROSS REFERENCE TO RELATED APPLICATIONS

The present application is being filed concurrently with U.S. application Ser. No. 12/636,174 entitled "Methods And Devices For Providing Access Through Tissue To A Surgical Site" and U.S. application Ser. No. 12/636,184 entitled "Methods And Devices For Providing Access Through Tissue To A Surgical Site," which are incorporated by reference herein in their entireties.

FIELD OF THE INVENTION

The present invention relates to methods and devices for providing access through tissue to a surgical site.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity.

A trocar is one type of access post that is commonly used to provide a minimally invasive pathway for accessing a surgical site. Trocars generally include a cutting assembly or obturator that is disposed within an outer cannula. The sharp distal end of the cutting assembly, with the cannula disposed therearound, is urged through the skin until it enters the anatomical cavity being penetrated. The cutting assembly is then withdrawn from the cannula, which remains in place to provide a passageway through which access to the anatomical cavity is provided for other surgical devices, e.g., laparoscopic instruments such as graspers, dissectors, scissors, retractors, etc.

While effective, there can be many disadvantages when using a typical trocar assembly. For example, numerous types of procedures using a typical trocar assembly involve insufflation of the abdominal cavity with $CO_2$ gas to increase interior space for a surgical procedure. This is often achieved using an additional port to allow gas to be passed into a body cavity to provide pressure therein to maintain insufflation of the cavity. Maintaining insufflation can be difficult because the trocar can extend a distance above the skin and surface through which it is inserted depending on the length of the trocar, which could create a gap through which insufflation fluid can escape. Additionally, the trocar could move relative to the tissue in which it is inserted, such as when instruments are inserted therethrough into the cavity, which could affect insufflation as well as interfere with proper positioning of the instruments. Insufflation can be made even more difficult before the body cavity is inflated as there are organs and other vital structures that can be directly adjacent the puncture site where the trocar assembly is inserted through the tissue, and it is desirable to prevent damage to these structures during insertion of the trocar.

Accordingly, there is a need for improved methods and devices for providing access through tissue to a surgical site.

SUMMARY OF THE INVENTION

The present invention generally provides methods and devices for providing access through tissue to a surgical site. In one embodiment, a modular access device is provided that includes a housing having a cannula extending distally therefrom, the housing and the cannula defining a working channel extending therethrough for receiving an instrument, at least one seal element disposed within the working channel and configured to form at least one of a seal around an instrument disposed through the working channel and a seal across the working channel when no instrument is disposed therethrough, and an anchor segment removably coupled to a distal end of the cannula.

In some embodiments, the cannula is formed from a plurality of segments, which can be polyaxially coupled to one another.

The anchor segment can have a variety of sizes, shapes, and configurations. The anchor segment can have a maximum outer diameter that is greater than a maximum outer diameter of the cannula. The anchor segment can optionally have at least one retention thread formed on an outer surface thereof. In some embodiments, the anchor segment can be movable between a first configuration in which the anchor segment has a first outer diameter and a second configuration in which the anchor segment has a second outer diameter that is greater than the first outer diameter. The anchor segment can be configured to move between the first configuration and the second configuration upon rotation of a distal end of the anchor segment. An engagement feature can be formed within the anchor segment and be configured to couple to a complementary engagement feature on an obturator. At least a portion of the anchor segment can be configured to collapse when the anchor segment moves from the first configuration to the second configuration. In some embodiments, the anchor segment can include a plurality of flexible wires spaced longitudinally apart from one another and configured to collapse when the anchor segment moves from the first configuration to the second configuration. A sleeve can be disposed over the plurality of flexible wires.

In another embodiment, a modular access device is provided that includes a housing having a cannula extending distally therefrom, the housing and the cannula defining a working channel extending therethrough for receiving an instrument. The cannula includes a plurality of segments removably coupled to one another. When the plurality of segments are mated, the plurality of segments are movable toward and away from one another along a longitudinal axis of the working channel to allow a length of the cannula to be adjusted. In some embodiments, the cannula can have a scallop-shaped external surface.

The modular access device can also include at least one seal disposed within the working channel and configured to form at least one of a seal around an instrument disposed through the working channel and a seal across the working channel when no instrument is disposed therethrough. In some embodiments, an anchor segment can be attached to a distal-most end of the cannula. The anchor segment can have a maximum outer diameter that is greater than a maximum outer diameter of the cannula.

The plurality of segments can have a variety of sizes, shapes, and configurations. For non-limiting example, the plurality of segments can be polyaxially coupled to one another and/or be mated to form a fluid tight seal therebetween. In some embodiments, each segment can include a biasing element and/or a flexion region. The biasing element can bias the plurality of segments toward one another. Each segment can include a bore formed therein, and the biasing element can include at least one radially-extending deflectable flange configured to engage the bore. The flexion region can be configured to allow a longitudinal length of the segment to be adjusted. In some embodiments, one of the plurality of segments can be removably coupled to the housing.

In another embodiment, a modular access device includes a housing having a cannula extending distally therefrom, the housing and the cannula defining a working channel extending therethrough. The cannula includes a plurality of segments movably coupled to one another. Each segment has a male member and a female member, and each segment includes a biasing feature that biases the male and female members into engagement with one another.

The modular access device can vary in any number of ways. The plurality of segments can be movable toward and away from one another when the segments are mated to allow a length of the cannula to be adjusted. A mating connection between each of the plurality of segments can form a fluid tight seal. The plurality of segments can be polyaxially coupled to one another.

The male and female members can each have a variety of sizes, shapes, and configurations. The male member can be configured to mate to the female member by snap-fit. The female member can optionally include an expandable opening. The female member can include a bore, and the biasing feature can include at least one radially-extending deflectable flange formed on the male member and configured to engage the bore. In some embodiments, the male member can include a ball, and the female member can include a socket.

In another aspect, a modular access system is provided that includes a housing configured to be positioned above an outer surface of a tissue, a cannula extending distally from the housing and configured to extend through an opening in the tissue, and a plurality of anchors of differing configurations. Each anchor is removably matable to a distal end of the cannula. The cannula can optionally be formed from a plurality of segments.

The modular access system can include any number of other components, such as at least one seal disposed within at least one of the housing and the cannula, with the at least one seal being configured to form at least one of a seal around an instrument disposed through the access device and a seal within the access device when no instrument is disposed therethrough. For another non-limiting example, the modular access system can include an obturator disposable through the housing and the cannula. At least one of the plurality of anchors can have an engagement feature formed therein, and the obturator can have as an engagement feature formed thereon and configured to mate with the engagement feature on the anchor. The obturator can optionally have a transparent distal tip.

In some embodiments, the anchor can be movable between a first configuration in which the anchor has a first outer diameter and a second configuration in which the anchor has a second outer diameter that is greater than the first outer diameter. The anchor can be moved between the first and second configurations in a variety of ways. For example, an obturator disposable through the housing and the cannula can be configured to rotate about a longitudinal axis of the obturator to move the anchor from the first configuration to the second configuration.

In another aspect, a surgical access device is provided that includes a housing having a cannula extending distally therefrom, and an adjustment mechanism coupled to the housing. The housing and the cannula define a working channel extending therethrough for receiving an instrument. The cannula is movable between an insertion configuration and a deployed configuration, and a biasing force biases the cannula to the deployed configuration. The adjustment mechanism is configured to adjust the biasing force.

The cannula can have a variety of sizes, shapes, and configurations. For non-limiting example, in the insertion configuration, the cannula can have a length that is greater than a length of the cannula in the deployed configuration and/or have a maximum outer diameter that is greater than a maximum outer diameter of the cannula in the deployed configuration. For another non-limiting example, the cannula can include a plurality of segments movably coupled to one another. In some embodiments, the adjustment mechanism can be selectively rotatable relative to the housing to adjust the biasing force. The cannula can optionally include a distal-most anchor, and rotation of the adjustment mechanism can be effective to expand the distal-most anchor.

The surgical access device can include any one or more additional components, such as a biasing element coupled to the cannula and configured to apply the biasing force to the cannula. The biasing element can include at least one cable extending through the cannula. The adjustment mechanism can be configured to adjust a length of the at least one cable to adjust the biasing force. For another non-limiting example, the surgical access device can include at least one seal element disposed within the working channel and configured to form at least one of a seal around an instrument disposed through the working channel and a seal across the working channel when no instrument is disposed therethrough.

In another embodiment, a surgical access device is provided that includes a housing having a cannula extending distally therefrom. The housing and the cannula define a working channel extending therethrough for receiving an instrument, and the cannula is movable between an insertion configuration and a deployed configuration. At least one biasing element coupled to the cannula is configured to apply a biasing force to the cannula to bias the cannula to the deployed configuration. An adjustment mechanism operatively coupled to the at least one biasing element is configured to adjust the biasing force. Optionally, the adjustment mechanism can be selectively rotatable relative to the housing to adjust the biasing force, and/or at least one seal element can be disposed within the working channel and be configured to form at least one of a seal around an instrument disposed through the working channel and a seal across the working channel when no instrument is disposed therethrough.

The cannula can have a variety of sizes, shapes, and configurations. The cannula can include a plurality of segments movably coupled to one another. In the insertion configuration, the cannula can have a length that is greater than a length of the cannula in the deployed configuration and/or have a maximum outer diameter in the insertion configuration that is greater than a maximum outer diameter of the cannula in the deployed configuration. In some embodiments, the cannula can include a distal-most expandable anchor. The distal-most expandable anchor can moves from an insertion configuration to an expanded configuration when the cannula is moved from the insertion configuration to the deployment configuration.

In some embodiments, the biasing element can include at least one cable extending through the cannula. The adjustment mechanism can be configured to adjust a length of the at least one cable to adjust the biasing force.

BRIEF DESCRIPTION OF THE DRAWINGS

The invention will be more fully understood from the following detailed description taken in conjunction with the accompanying drawings, in which:

FIG. 2 is a side cross-sectional view of the surgical access device of FIG. 1;

FIG. 3 is a side cross-sectional view of one of the segments of FIG. 1;

FIG. 4 is a side cross-sectional view of another embodiment of a segment;

FIG. 7 is a side cross-sectional view of the anchor of FIG. 1 with the anchor in an undeployed configuration and with the obturator of FIG. 1 being inserted into the anchor;

FIG. 8 is a side cross-sectional view of the anchor and the obturator of FIG. 7 with the obturator keyed to the anchor and with the anchor in a deployed configuration;

FIG. 9 is a perspective, partially transparent view of the anchor of FIG. 8 in the deployed configuration;

FIG. 27 is a side cross-sectional view of the cannula of FIG. 25 having a sleeve disposed therearound and showing a proximal segment being removable from the cannula;

FIG. 28 is a side cross-sectional view of another embodiment of a surgical access device positioned within an opening in tissue, having a housing with a cannula distally extending therefrom, and having a surgical instrument inserted through a working channel of the surgical access device, the cannula including a plurality of segments movably coupled to one another, having an anchor in a deployed configuration at a distal end thereof, and the cannula having a sleeve formed of a plurality of discrete members disposed therearound;

FIG. 36 is a side cross-sectional view of the segment and the anchor of FIG. 35 having an obturator inserted through a proximal end of a working channel defined by the segment and the anchor, the obturator having an expander tool disposed within an inner passageway thereof;

FIG. 37 is a side cross-sectional view of the segment and the anchor of FIG. 36 with a distal tip of the obturator located distal to the anchor and the expander tool disposed within the anchor;

FIG. 38 is a side cross-sectional view of the segment and the anchor of FIG. 37 with the expander tool expanding a distal portion of the obturator to form a compression lock between the obturator and the anchor;

DETAILED DESCRIPTION OF THE INVENTION

Figure 1:
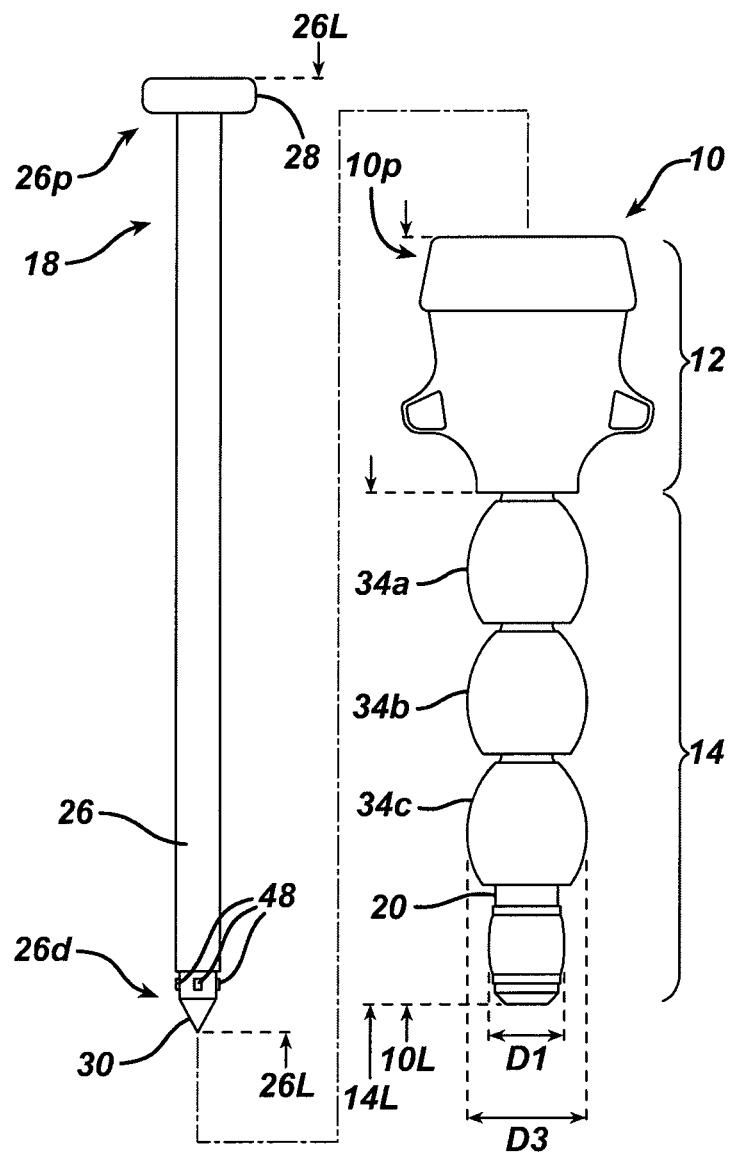
FIG. 1 is a side view of one embodiment of a surgical access device having a housing with a cannula distally extending therefrom, the cannula including a plurality of segments movably and removably coupled to one another and having an anchor at a distal end thereof, and a side view of one embodiment of an obturator receivable in a working channel of the surgical access device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are disclosed for providing surgical access into a body cavity. In general, the methods and devices provide access through tissue to a body cavity underlying the tissue using a surgical access port configured to be secured within an opening in the tissue to allow access therethrough. In an exemplary embodiment, a surgical access port is provided that has an adjustable longitudinal length. Because tissue thicknesses can vary, having a surgical access port with an adjustable longitudinal length of the surgical access port can allow the surgical access port to be appropriate for use with a variety of tissue thicknesses and can facilitate secure positioning of the surgical access port within tissue. A surgical access port with an adjustable longitudinal length can minimally extend into a body cavity underlying the tissue where the surgical access port could harm body structures within the body cavity and/or interfere with instruments performing a surgical procedure in the body cavity. The surgical access port's longitudinal length can be selectively adjusted after it is positioned within an opening in tissue, thereby allowing the longitudinal length to be tailored to a particular tissue's thickness with a reduced or nonexistent need to guess or pre-measure a tissue's thickness. In some embodiments, an anchor can be coupled to a distal end of the surgical access port to help secure the surgical access port within the tissue opening by engaging a distal side of the tissue, e.g., tissue facing the body cavity. The anchor can be configured to be deployed when the surgical access port's longitudinal length is selectively adjusted, which can quicken setup of the surgical access port. Optionally, the anchor can be removably coupled to the distal end of the surgical access port, thereby allowing any one of a plurality of anchors to be selectively coupled thereto based on a particular surgical procedure, a particular tissue's thickness, a particular body cavity in which it will be inserted, etc.

The various surgical access devices can include an elongate tubular member, cannula, or other member for forming a pathway through tissue (hereinafter generally referred to as a cannula). The cannula can extend distally from a proximal housing configured to be at least partially disposed outside a patient's body, and it can be configured to be positioned within an opening in a patient's body, such as through skin. The proximal housing can include one or more sealing ports that can each define working channels extending through the housing and aligned with the cannula. A person skilled in the art will appreciate that the cannula can include one or more sealing ports, in addition or in alternative to one or more sealing ports in the housing. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Publication No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

In use, and as also further discussed below, the surgical access devices disclosed herein can provide access to a patient's body cavity. At least a portion of the cannula can be positionable within an opening in a patient's body such that a distal portion of the cannula extends into a patient's body cavity and at least a portion of the housing is positioned adjacent to the patient's skin on an exterior of the patient's body. In some embodiments, the device may not include a housing, in which case at least a proximal portion of the cannula can be positioned adjacent to the patient's skin on an exterior of the patient's body when another portion of the cannula is positioned within an opening in a patient's body. A lumen in the cannula and the housing can form a pathway through the opening in a patient's body so that surgical instruments can be inserted from outside the body to an interior body cavity. The elasticity of the skin of the patient can assist in the retention of the cannula in the body opening or incision made in the body. The cannula can be placed in any opening within a patient's body, whether a natural orifice or an opening made by an incision. In one embodiment, the cannula can be substantially flexible so that it can easily be maneuvered into and within tissue as needed. In other embodiments, the cannula can be substantially rigid or substantially semi-rigid.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough, at least one channel seal or zero-closure seal that seals the working channel created by the sealing port when no instrument is disposed therethrough, or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment.

In an exemplary embodiment illustrated in FIGS. 1 and 2, a surgical access device 10 can include a housing 12 and a cannula 14 distally extending therefrom. The housing 12 and the cannula 14 can define a working channel 16 extending through the device 10 and being configured to slidably and removably receive an obturator 18 and/or any number of other surgical instruments therein. Generally, the device 10 can be configured to be positioned within an opening in tissue to provide access to a surgical site and allow a surgical instrument to be inserted through the working channel 16 to perform a surgical procedure at the surgical site. An anchor or anchor segment 20, generally referred to as an "anchor," can be located at a distal end 14d of the cannula 14 and can assist in securing the device 10 within an opening in tissue, as discussed further below. The anchor 20 can be configured to self-deploy, or the obturator 18 can be configured to deploy the anchor 20, as also discussed further below. As illustrated, the cannula 14 can include a plurality of beads, modules, or segments 34a, 34b, 34c, generally referred to as "segments," movably coupled together such that the cannula 14 can bend and can adjust in longitudinal length. Generally, the segments 34a, 34b, 34c can allow the cannula 14 to be configured as an axially-expandable, articulating tubular member configured to be securely positioned within tissue of any thickness, e.g., in a range of about 1-7 cm thick, and articulate therein to improve access to a body cavity underlying the tissue.

The housing 12, the cannula 14, the obturator 18, and the anchor 20 can each have a variety of sizes, shapes, and configurations. Generally, the housing 12 can be configured to provide a pathway for receiving a surgical instrument such the obturator 18, an endoscope, a retractor, a dissector, a cutting instrument, etc. Exemplary housing configurations are described in more detail in U.S. Pat. No. 6,017,356 entitled "Method For Using A Trocar For Penetration And Skin Incision", issued on Jan. 25, 2000, U.S. Patent Publication No. 2004/0230161 entitled "Trocar Seal Assembly," filed on Mar. 31, 2004, and U.S. Patent Publication No. 2007/0185453 entitled "Conical Trocar Seal," filed on Oct. 15, 2003, which are hereby incorporated by reference in their entireties.

The housing 12 can include proximal and distal sealing elements 22a, 22b configured to provide at least one of a channel seal and an instrument seal. Although the housing 12 in the illustrated embodiment includes two sealing elements 22a, 22b, a person skilled in the art will appreciate that the device 10 can include any number of sealing elements and that in addition or in alternative to at least one sealing element in the housing 12, the cannula 14 can include one or more sealing elements.

The sealing elements 22a, 22b can have a variety of sizes, shapes, and configurations. As shown in the illustrated embodiment, the distal sealing element 22b can include a duckbill seal that provides a channel seal, and the proximal seal 22a can include a septum seal that provides an instrument seal. In use, when a surgical instrument is passed through the proximal seal 22a, the proximal seal 22a can engage and form a seal around an outer surface of the instrument to thereby prevent passage of fluids and gas through the seal 22a. When no instrument is disposed therethrough, the proximal seal 22a will generally not form a seal in the working channel 16. A person skilled in the art will appreciate that while an instrument seal in the form of a septum seal is shown, any seal can be used. Exemplary instrument seal configurations are described in more detail in U.S. patent application Ser. No. 12/399,482 entitled "Methods And Devices For Providing Access Into A Body Cavity," filed Mar. 6, 2009, U.S. Patent Publication No. 2004/0230161 entitled "Trocar Seal Assembly," filed on Mar. 31, 2004, and U.S. Patent Publication No. 2007/0185453 entitled "Conical Trocar Seal," filed on Oct. 15, 2003, which are hereby incorporated by reference in their entireties. When the instrument is further inserted through the distal seal 22b, the instrument can open the distal seal 22b and pass into the cannula 14. A person skilled in the art will appreciate that while a channel or zero-closure seal in the form of a duckbill seal is shown for the distal seal 22b, any seal, e.g., duckbill seals, cone seals, flapper valves, gel seals, diaphragm seals, lip seals, iris seals, non-linear sealing elements such as sealing elements with an S-shaped opening, etc., can be used. Generally, a zero-closure seal can be configured to form a seal in a working channel when no instrument is disposed therethrough to thus prevent the leakage of insufflation gases delivered through the surgical access device to the body cavity. A duckbill seal can generally have opposed flaps that extend at an angle toward one another in a distal direction and that come together at a distal end to form a seal face. The opposed flaps can be movable relative to one another to allow the seal face to move between a closed position, in which no instrument is disposed therethrough and the seal face seals the working channel of the surgical access device, and an open position in which an instrument is disposed therethrough. A duckbill seal can include various other features, as described in more detail in U.S. Patent Publication No. 2009/0005799, entitled "Duckbill Seal with Fluid Drainage Feature," filed on Jun. 29, 2007, which is hereby incorporated by reference in its entirety. In addition, the seal face of the duckbill seal can be in any nonlinear shape or configuration known in the art, for example in an S-shaped configuration, as described in more detail in U.S. Pat. No. 5,330,437, entitled "Self Sealing Flexible Elastomeric Valve and Trocar Assembly for Incorporating Same," filed Nov. 12, 1993, which is hereby incorporated by reference in its entirety.

The housing 12 can include an insufflation port 24 extending from a sidewall of the housing 12, although a person skilled in the art will appreciate that the insufflation port 24 can be located elsewhere in the housing 12 or in other locations. A person skilled in the art will also appreciate that the device 10 can include any number of insufflation ports and that an insufflation port can have a variety of configurations. Generally, the insufflation port 24 can be configured to pass an insufflation fluid through a flexible insufflation tube and into an insufflation orifice of the insufflation port 24 where the fluid can flow through the working channel 16 and into a body cavity. A stopcock can control fluid flow through the insufflation tube. In an exemplary embodiment, a surgical access device kit can include multiple modular stopcocks, e.g., an insufflation/vent three-way version, a twist to activate version, a spring loaded version, etc.

The housing 12 can fixedly or removably attach to the cannula 14 in a variety of ways. In the illustrated embodiment, a distal end 12d the housing 12 and a proximal end 14p of the cannula 14 include complementary mating features configured to movably and removably mate the housing 12 and the cannula 14 together. Although the mating features can have a variety of configurations, e.g., welded elements, snap-fit elements, threads, etc., in the illustrated embodiment the housing's distal end 12d includes a female member 32, e.g., an opening, socket, or cavity, configured to receive a male member, e.g., a protrusion, ball, or knob, at the cannula's proximal end 14p configured to be movably disposed in the female member 32. In this way, the cannula 14 can move relative to the housing 12, e.g., with the male member being rotatable within the female member 32, which can facilitate positioning of the cannula 14 within a tissue opening. The housing's female member 32 can have a variety of sizes, shapes, and configurations, such as shown in FIG. 2 with the female member 32 including a distal tapered portion 32d tapering outwardly in a distal direction to provide adequate space for the cannula 14 to move, as discussed further below, and a proximal pivot socket portion 32p configured to receive the cannula's male member therein by interference or snap fit. The proximal pivot socket portion 32p can have a rounded shape complementary to a rounded shape of the cannula's male member to allow the male member to freely rotate therein to allow polyaxial movement of the cannula 14 relative to the housing 12.

The cannula's male member can have a variety of sizes, shapes, and configurations, as can the cannula 14. Generally, the cannula 14 can be formed from a plurality of segments 34a, 34b, 34c movably coupled together with proximal ends of each of the segments 34a, 34b, 34c including a male member 36a, 36b, 36c configured to be received in a distal female member 38a, 38b, 38c of another segment 34a, 34b, 34c or in the distal female member 32 of the housing 12. Although the cannula 14 is illustrated with three segments 34a, 34b, 34c, the cannula 14 can include any number of segments. As shown in FIG. 2, the male member 36a of the proximal-most one of the segments 34a, illustrated as a standalone element in FIG. 3, can be configured to be seated in the housing's female member 32 by interference or snap fit to mate the cannula 14 to the housing 12.

The complementary mating features of the housing 12 and the cannula 14 can also be configured to allow the housing 12 to be removable from the cannula 14, e.g., through unthreading, by unsnapping the proximal-most segment's male member 36a from the housing's female member 32, etc., thereby allowing housings and cannulas of various sizes and including various features to be mixed and matched as appropriate for a particular surgical application. Similarly, the complementary mating features of the cannula's segments 34a, 34b, 34c can be configured to allow any number of segments to be added to or removed from the cannula 14, thereby allowing the cannula's longitudinal length 14L to be adjusted as desired for a particular surgical application. In other words, the segments 34a, 34b, 34c can be modular. Optionally, a plurality of segments, anchors, and/or housings can be provided as part of a kit that can be assembled and/or disassembled to form a surgical access device tailored for a particular surgical application.

The segments 34a, 34b, 34c can have a variety of sizes, shapes, and configurations, and can be same or different from any of the other segments 34a, 34b, 34c. In the illustrated embodiment, each of the segments 34a, 34b, 34c is identical.

The segments 34a, 34b, 34c can be composed of any one or more flexible and/or rigid materials, although the segments 34a, 34b, 34c in the illustrated embodiment are flexible and are formed of at least one flexible, puncture-resistant polymer, e.g., isoprene, polyethylene, and polypropylene. Optionally, the proximal-most segment 34a and/or the distal-most segment 34c can be formed of a material more rigid than a material forming one or more segments 34b connected therebetween, which can help facilitate insertion of the cannula 14 through a tissue opening and retention of the cannula 14 therein.

Generally, referring to the proximal-most segment 34a illustrated in FIG. 3, the segment 34a can include a bottle-shaped body with a bulbous, spherical, distal portion including the female member 38a therein, a proximal head portion including the male member 36a, and a smaller-diameter, cylindrical, proximal neck portion extending between the proximal and distal portions and configured to axially move into and out of an adjacent segment's female member. In this way, when multiple segments are attached together, the cannula 14 can have a scallop-shaped external surface, as illustrated in FIGS. 1 and 2. In other exemplary embodiments, segments forming a cannula can each have a cube-shaped, rectangular-shaped, or cylindrically-shaped distal portion such that the cannula can have a substantially constant outer diameter at least when the cannula is in a compressed configuration.

An external surface of the segment 34a, e.g., on the body, can optionally include at least one gripping feature (not shown) formed thereon, e.g., a textured surface, at least one spiraling thread, etc., that can be configured to facilitate the segment's retention within tissue. A bore or lumen 44 can extend between proximal and distal ends 34p, 34d of the segment 34a. A distal portion of the bore 44 can define the segment's female member 38a, and a proximal portion of the bore 44, e.g., within the male member 34a, can taper radially outward to facilitate insertion of a surgical instrument therethrough. Collectively, the bores 44 of the segments 34a, 34b, 34c can axially align with one another along a longitudinal axis A of the device 10 to form a portion of the device's working channel 16.

The segments' female members 38a, 38b, 38c can have a variety of sizes, shapes, and configurations, such as shown in FIGS. 2 and 3 with the female members 38a, 38b, 38c each including a distal tapered portion 38d tapering outwardly in a distal direction to facilitate bending and axial expansion of the cannula 14, and a proximal pivot socket portion 38p configured to receive the another segment's male member or a male member 40 of the anchor segment 20. In this way, the cannula 14 can include the segments 34a, 34b, 34c movably linked together with the anchor segment 20 movably linked to the distal-most one of the segments 34c. Similar to the housing's proximal pivot socket portion 32p, the segments' female members 38a, 38b, 38c can each have a rounded shape complementary to rounded shapes of the segments' male members 36a, 36b, 36c such that each male member can rotate within its respective female member, thereby allowing free movement of each of the segments 34a, 34b, 34c and the anchor segment 20 relative to a remainder of the cannula 14 and to the housing 12. The female members 32, 38a, 38b, 38c can be expandable to facilitate removal and insertion of a male member.

FIG. 4 illustrates another exemplary embodiment of a segment 34" in which the segment's female member 38" has a square or rectangular proximal pivot socket portion 38p", which can help facilitate longitudinal movement of another segment's male member, which can have a proximal square or rectangular portion similar to the segment's male member 36".

Referring again to FIGS. 1-3, as mentioned above, the segments 34a, 34b, 34c can be movably coupled together such that the segments 34a, 34b, 34c can polyaxially move relative to one another. The segments 34a, 34b, 34c can also be longitudinally movable relative to one another along the device's and working channel's longitudinal axis A such that the longitudinal length 10L of the device 10 can be adjusted, and more particularly such that a longitudinal length 14L of the cannula 14 can be adjusted. The cannula 14 can be configured to move between a compressed configuration in which the cannula 14 has a minimum longitudinal length 14L and an expanded configuration, shown in FIGS. 1 and 2, in which the cannula 14 has a longitudinal length 14L greater than its minimum longitudinal length 14L. The cannula 14 can be biased to the compressed configuration such that when positioned within a tissue opening, the cannula 14 can move to a longitudinal length approximating a longitudinal length of the tissue opening. In this way, the device 10 can be securely positioned within tissues of varying thicknesses while reducing chances of damaging or interfering with any matter within a body cavity to which the device 10 provides access.

To facilitate longitudinal length adjustment of the cannula 14, each of the segments 34a, 34b, 34c can include one or more flexible biasing elements 42a, 42b, 42c. In the illustrated embodiment, shown in FIGS. 2 and 3, each of the segments 34a, 34b, 34c includes two biasing elements 42a, 42b, 42c, a proximal radially-extending deflectable flange having a first diameter and a distal radially-extending deflectable flange having a second, larger diameter, but the segments 34a, 34b, 34c can include any number of biasing elements. The biasing elements 42a, 42b, 42c can extend circumferentially or around a perimeter of their respective segments 34a, 34b, 34c such that when the biasing element of one segment is inserted into the bore of an adjacent segment, that biasing element engages a perimeter of the bore of the adjacent segment so as to form a fluid-tight seal between those two segments. In this way, a fluid-tight seal can be formed between each of the segments 34a, 34b, 34c, between the housing 12 and the proximal-most segment 34a, and between the distal-most segment 34c and the anchor 20 such that the working channel 16 can be fluid-tight to prevent escape of insufflation fluid and to prevent entry or exit of other unwanted material into or out of the cannula 14.

One or more of the segments 34a, 34b, 34c can optionally include a channel seal, e.g., a lip seal, which can also help prevent escape of insufflation fluid and to prevent entry or exit of other unwanted material into or out of the cannula 14. The channel seal can be located anywhere within the segment's inner lumen, such as at a proximal end thereof, e.g., within the male member of the segment. Optionally, a protective sleeve, discussed further below, can be disposed over an external surface of the cannula 14 to further facilitate sealing of the cannula 14 as well as reduce tissue trauma and facilitate insertion and removal of the cannula 14 from tissue.

Figure 5:
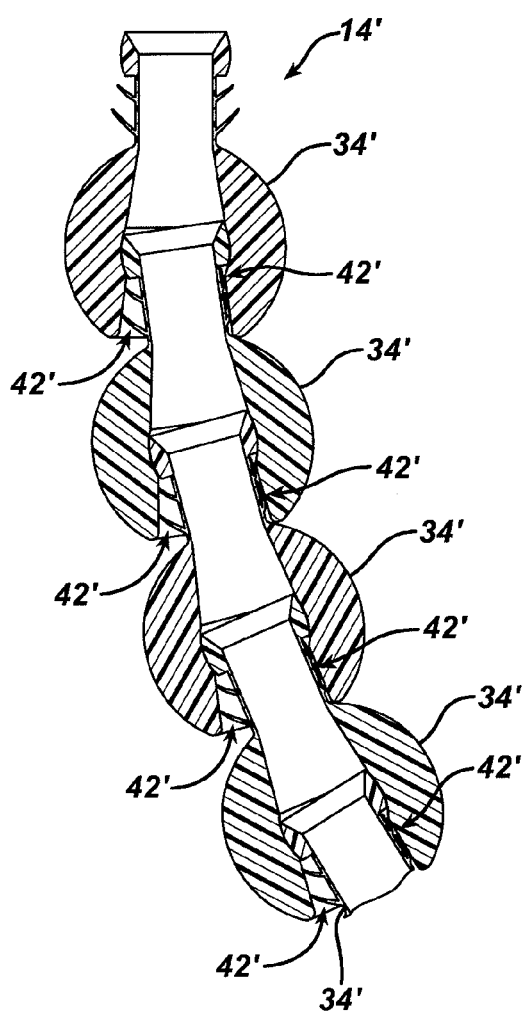
FIG. 5 is a side, cross-sectional, partial view of another embodiment of a cannula including a plurality of segments movably and removably coupled to one another, the cannula being in a curved position.

The biasing elements 42a, 42b, 42c can also be configured to be compressible to allow bending of the cannula 14. As shown in another exemplary embodiment in FIG. 5 showing a portion of a cannula 14' including five movably coupled segments 34' each having two flanges or biasing elements 42', the biasing elements 42' can be configured to compress in a direction of cannula bending, e.g., to the right as illustrated in FIG. 5, while maintaining a fluid-tight seal, e.g., maintaining contact within segment bores in which they are respectively disposed.

Referring again to FIGS. 1-3, the biasing elements 42a, 42b, 42c can be configured to be contained within an adjacent female member and to bias their respectively associated male and female members into engagement with one another, e.g., the biasing elements 42a of the proximal-most segment 34a biasing the proximal-most segment's male member 36a into engagement with the housing's female member 32, the biasing elements 42c of the distal-most segment 32c biasing the segment's male member 36c into engagement with the middle segment's female member 38b, etc. In other words, the biasing elements 42a, 42b, 42c can be configured to bias the cannula 14 to the compressed or default configuration. With the cannula 14 in the compressed configuration, the biasing elements 42a, 42b, 42c can each be in a default configuration, as illustrated in FIG. 3 showing the biasing elements 42a of the proximal-most segment 34a in the default configuration. In the default configuration, the biasing elements 42a, 42b, 42c can extend radially and substantially perpendicularly outward from their respective segment bodies. The biasing elements 42a, 42b, 42c can be configured to move from the default configuration to allow distal movement of their respective segments 34a, 34b, 34c such that the longitudinal length 14L of the cannula 14, and hence the longitudinal length 10L of the device 10, increases. In other words, the biasing elements 42, 42b, 42c can be configured as springs that compress and expand to allow axial compression and expansion of the cannula 14. FIG. 2 illustrates the cannula 14 in the expanded configuration with each of the biasing elements 42a, 42b, 42c bent and with each of the segments 34a, 34b, 34c moved in a distal direction. Although FIG. 2 illustrates each of the segments 34a, 34b, 34c moved and each of the biasing elements 42a, 42b, 42c bent, any one or more of the biasing elements 42a, 42b, 42c can bend to allow any one or more of the segments 34a, 34b, 34c to move to adjust the cannula's longitudinal length 14L.

The cannula 14 can be configured to be held or locked in the expanded configuration when positioned in a tissue opening and to dynamically move toward the compressed configuration, and possibly all the way to the compressed configuration, to reduce its longitudinal length 14L after being inserted into the tissue opening. In this way, when the device 10 is positioned with an opening in tissue, the cannula 14 can be in the expanded configuration and then move into the compressed configuration to adjust the cannula 14 to the tissue's thickness. In an exemplary embodiment, the obturator 18 can be configured to hold the cannula 14 in the expanded configuration and to be at least partially removed from the working channel 16 to allow the cannula 14 to move toward the compressed configuration. However, as mentioned above, any instrument can be disposable through the working channel 16 defined by the housing 12 and the cannula 14, and any instrument can be configured to facilitate adjustment of the cannula's longitudinal length 14L.

The obturator 18 can have a variety of sizes, shapes, and configurations. Exemplary embodiments of an obturator are described in more detail in U.S. Pat. No. 6,017,356 entitled "Method For Using A Trocar For Penetration And Skin Incision," issued on Jan. 25, 2000, and U.S. Patent Publication No. 2007/0260273 entitled "Endoscopic Translumenal Surgical Systems," filed May 8, 2006, which are hereby incorporated by reference in their entireties.

Generally, the obturator 18 can include an elongate shaft 26 having a proximal end 26p including a handle 28 configured to be handheld outside a patient's body and a distal end 26d with a tip 30 configured to be inserted through tissue. The obturator 18 in the illustrated embodiment is a solid member and with at least the shaft 26 being substantially flexible, but the obturator 18 can be substantially rigid and/or hollow. The shaft 26 can be made substantially flexible using various techniques. For non-limiting example, the shaft 26 can be formed from a flexible material, and/or it can include one or more features formed therein to facilitate flexibility, such as a plurality of cut-outs or slots. In other embodiments, the shaft 26 can be formed from a plurality of linkages that are movably coupled to one another. The shaft 26 can also include regions that vary in flexibility. For non-limiting example, certain portions of the shaft 26, such as the distal portion, can be more rigid than other portions of the shaft 26, such as the proximal portion, to facilitate insertion of the obturator 18 through tissue alone or disposed within the cannula 14. Varying flexibility of the shaft 26 can be achieved in a variety of ways as will be appreciated by a person skilled in the art, such as by forming the shaft 26 from different materials, varying the diameter or thickness of the shaft 26, etc. The shaft 26 can also include other features to facilitate use, such as one or more spiral wires embedded therein and configured to preventing kinking of the shaft 26.

The size and shape of the shaft 26 can vary, but as shown in FIG. 1, the shaft 26 can have a longitudinal length 26L greater than a longitudinal length 10L of the device 10 such that the obturator 18 can be inserted through the device's working channel 16 with the shaft's proximal end 26p located proximal to the housing 12 and the shaft's distal end 26d located distal to the anchor 20. The obturator's handle 28 can have a maximum diameter greater than a diameter of at least a proximal-most end of the working channel 16, thereby preventing the obturator 18 from being fully inserted into the device 10 through a proximal end 10p thereof.

The obturator's distal tip 30 can also have a variety of shapes, sizes, and configurations. Generally, the tip 30 can be configured to penetrate tissue. The tip 30 can be composed of any one or more flexible and/or rigid materials, although the tip 30 in the illustrated embodiment is rigid, e.g., composed of stainless steel, titanium, etc., to help the tip 30 penetrate tissue. In an exemplary embodiment, the tip 30 can be transparent to allow visualization therethrough. For non-limiting example, an endoscope (not shown) can be proximally inserted into a hollow obturator and be disposed within the hollow obturator and provide visualization through the obturator's clear distal tip. The tip 30 can be integrally formed with a reminder of the shaft 26, or it and/or the tip 30 can be removably or fixedly attached to the shaft 26, e.g., through an interference fit, an adhesive, ultrasonic welding, etc. The tip 30 can have a variety of shapes, e.g., conical (as shown in FIG. 1), triangular, rectangular, rounded, etc. The tip 30 can include one or more features to help it to penetrate tissue, e.g., a tapered shape, a beveled edge (including a chamfered edge), a pointed needle, an electronic cutter, a sharp cutting blade, etc. Various exemplary configurations for the tip 30 are described in more detail in previously mentioned U.S. Patent Application No. 2007/0260273 entitled "Endoscopic Translumenal Surgical Systems," filed May 8, 2006.

Figure 6:
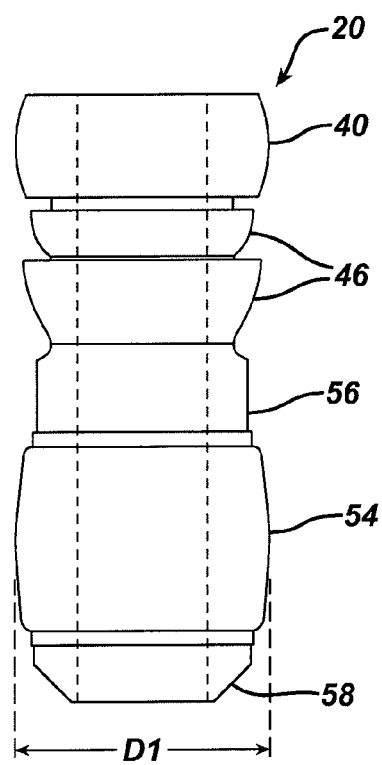
FIG. 6 is a side view of the anchor of FIG. 1.
Figure 10:
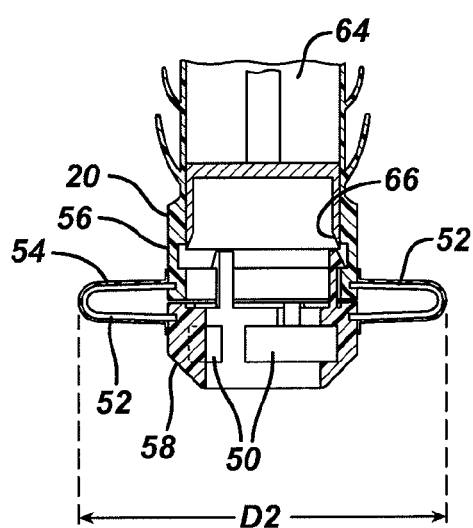
FIG. 10 is a side cross-sectional view of the anchor of FIG. 8 in the deployed configuration with the obturator removed therefrom.

The distal end 26d of the obturator 18 can also be configured to engage the anchor 20 to help move the cannula 14 between the expanded and compressed configurations and to facilitate deployment of the anchor 20. In other words, the obturator 18 and the anchor 20 can be configured to be keyed together. As illustrated in FIGS. 1, 2, and 6, the obturator 18 and the device 10 can include an engagement and release mechanism to key to each other. The engagement and release mechanism can include a bayonet latch mechanism. At least one bayonet foot or pin, e.g., a plurality of radially arranged bayonet feet or pins 48 spaced equidistantly or any other distance apart, can extend any length from an outer perimeter of the obturator 18, e.g., from an outer sidewall of the obturator 18, and the pins 48 can be configured to engage corresponding slots 50 formed in an inner circumferential surface of the anchor 20. The slots 50 can have any shape and size and can be the same as or different from any other of the slots 50. As discussed further below, the slots 50 can each include a vertically-extending portion in which the pins 48 can be proximally inserted and a laterally-extending portion in which the pins 50 can laterally slide. The pins 48 can have any shape and size and can be the same as or different from any other of the pins 48. The pins 48 can be configured to be lowered into the vertically-extending portion of the slots 50 in the anchor 20 and if identical, as in the illustrated embodiment, can be interchangeably lowered into any of the slots 50. Exemplary embodiments of bayonet latch mechanisms and other engagement and release features are described in more detail in U.S. patent application Ser. No. 12/399,482 entitled "Methods and Devices for Providing Access to a Body Cavity" filed on Mar. 6, 2009, and U.S. patent application Ser. No. 12/512,542 entitled "Methods and Devices for Providing Access Into a Body Cavity" filed on Jul. 30, 2009, which are hereby incorporated by reference in their entireties.

With the obturator 18 disposed in the working channel 16 and the bayonet pins 48 engaging their corresponding anchor slots 50, the obturator 18 can be moved distally relative to the device 10 to distally move the anchor 20 relative to at least the device's housing 12, thereby increasing the device's longitudinal length 10L by increasing the cannula's longitudinal length 14L. In other words, distal movement of the obturator 18 relative to the device 10 can flex one or more of the biasing elements 42a, 42b, 42c, 46 to move one or more of the segments 34a, 34b, 34c and/or the anchor 20 along the device's longitudinal axis A to change the device's longitudinal length 10L. The cannula 14 can alternatively or additionally be moved by hand between the expanded and compressed configurations. For clarity, the obturator 18, a hand, and/or other member holding the cannula 14 in the expanded configuration is not shown in FIG. 2.

The obturator 18 can also be configured to rotate about a longitudinal axis A2 of the obturator 18, which is the same as the longitudinal axis A of the working channel 16, when the obturator 18 is disposed therein, to deploy the anchor 20, as discussed further below.

The anchor 20, also illustrated in FIGS. 6-10, can be configured to be coupled to the distal-most one of the segments 34c and can have a variety of sizes, shapes, and configurations. Although the anchor 20 can be fixedly or removably attached to the cannula 14, in the illustrated embodiment, the anchor 20 is removably mated to the distal-most one of the segments 34c by interference or snap fit. As mentioned above, the proximal male member 40 of the anchor segment 20 can be received within the distal-most one of the segments' female member 38c to movably couple the anchor segment 20 thereto such that the anchor segment 20 can polyaxially and longitudinally move relative thereto similar to movement discussed above regarding the segments 34a, 34b, 34c. The anchor 20 can also include one or more biasing elements 46 configured and used similarly to the biasing elements 42a, 42b, 42c of the segments 34a, 34b, 34c, although the anchor's biasing elements 46 need not be identical to the segments' biasing elements 42a, 42b, 42c.

The anchor 20 can be configured to change shapes to facilitate securement of the device 10 within tissue. As in the illustrated embodiment, the anchor 20 can be configured to move between a first configuration, shown in FIGS. 1, 2, and 6, in which the anchor 20 has a first outer diameter D1, and a second configuration, shown in FIGS. 8 and 9, in which the anchor 20 has a second, larger outer diameter D2. The first outer diameter D1 can be equal to or less than a maximum outer diameter D3 of the cannula 14, while the second outer diameter D2 can be greater than the cannula's maximum outer diameter D3. Because a tissue opening in which the device 10 is positioned generally has a diameter substantially equal to the cannula's maximum outer diameter D3, the larger second outer diameter D2 can help prevent the anchor 20 from proximally advancing into the tissue opening.

The anchor 20 can include a proximal rim 56 and a distal rim 58 having an expandable mid-portion extending therebetween. The expandable mid-portion can have a variety of configurations, such as shown in the illustrated embodiment with a plurality of extending flexible cables, strings, threads, bands, ribbons, strips, or wires 52, generally referred to as "wires," spaced longitudinally apart from one another and extending between the rims 56, 58 with terminal ends of each of the wires 52 attached to the proximal and distal rims 56, 58, as shown in FIGS. 2 and 7. The proximal and distal rims 56, 58 can each include a rigid ring-shaped member as in the illustrated embodiment, but they can each have a variety of sizes, shapes, and configurations. The wires 52 can each extend substantially parallel to the longitudinal axis A of the working channel 16 when the anchor 20 is in the first configuration, as shown in FIGS. 1, 2, and 7. The wires 52 can be radially arranged and spaced equidistantly or any other distance apart from one another, and can be configured to collapse when the anchor 20 moves from the first configuration to the second configuration. Optionally, a flexible outer sheath 54 can be disposed around the wires 52 to help protect the wires 52 and prevent the wires 52 from snagging on tissue or other matter. The sheath 54 can optionally include a gripping feature (not shown), e.g., a textured surface, a non-slip coating, etc., configured to help grip tissue and reduce slippage of the anchor 20 against the tissue when the anchor 20 is deployed and abuts the tissue.

One or more longitudinal posts or clips 60, generally referred to as "clips," can extend proximally from the distal rim 58 and can be configured to engage a circumferential channel or groove 62, generally referred to as a "groove," formed in the proximal rim 56, as discussed further below. The anchor 20 includes three clips 60, but it can include any number of clips. The clips 60 and the groove 62 can have any size, shape, and configuration. As in the illustrated embodiment, the clips 60 can each include a longitudinally extending bar having a radially extending proximal protrusion 60p configured to engage the groove 62 and lock the clip 60 therein.

In use, the anchor 20 can be in the first configuration having the smaller diameter D1 when the device 10 is inserted through tissue, and the anchor 20 can be moved to the second configuration having the larger diameter D2 after the anchor 20 is located in a body cavity underlying the tissue. In this way, the anchor 20 can expand to engage a distal surface of the tissue facing the body cavity to help compress tissue between the anchor 20 and the housing 12, with the cannula 14 extending through the tissue opening therebetween. Because the deployed anchor 20 with the second outer diameter D2 can be larger than the cannula's maximum outer diameter D3, the anchor 20 can be prevented from being drawn proximally into the tissue opening having substantially the same diameter as the cannula's maximum outer diameter D2.

The anchor 20 can be moved between the first and second configurations in a variety of ways. In one exemplary embodiment, the anchor can include a shape memory material and be configured to automatically deploy. Exemplary embodiments of anchors including a shape memory material and being configured to automatically deploy are described in more detail in U.S. patent application Ser. No. 12/636,205 entitled "Methods And Devices For Providing Access Through Tissue To A Surgical Site," filed Dec. 11, 2009, and in U.S. patent application Ser. No. 12/636,232 entitled "Methods And Devices For Providing Access Through Tissue To A Surgical Site," filed Dec. 11, 2009, which are hereby incorporated by reference in their entireties.

As mentioned above, in the illustrated embodiment, the obturator 18 can be configured to move the anchor 20 between the first and second configurations. The obturator 18, with the anchor 20 keyed thereto through engagement of the bayonet pins 48 and the slots 50, can be rotated in a first direction, e.g., a clockwise direction, relative to the anchor 20, thereby causing the bayonet pins 48 to travel laterally within the slots 50, e.g., within the laterally-extending portion of the slots 50 away from the vertically-extending portion of the slots 50, to a position in which the pins 48 abut terminal ends of the slots 50, thereby locking the obturator 18 to the anchor 20. One or more of the slots 50 can angle proximally or distally (not shown) at their respective terminal ends such that the bayonet pins 48 can proximally or distally slide and snap into the terminal ends to help ensure that the bayonet pins 48 fully slide through the slots 50 to lock the obturator 18 to the anchor 20. In the illustrated embodiment, the bayonet pins 48 can move either clockwise or counterclockwise to lock the obturator 18 to the anchor 20 because the laterally-extending portions of the slots 50 extend in both directions from the vertically-extending portions of the slots 50. In some embodiments, the laterally-extending portions of the slots 50 can extend in only one direction from the vertically-extending portions of the slots 50.

With the obturator 18 locked to the anchor 20, e.g., with the bayonet pins 48 misaligned from the vertically-extending portion of the slots 50, the obturator 18 can be pulled proximally relative to the device 10, as shown in FIG. 8, thereby pulling the distal rim 58 of the anchor 20 toward the proximal rim 56 and expanding the wires 52 radially outward to change the anchor's shape. The obturator 18 can be optionally rotated about the working channel's axis A when the obturator 18 is pulled proximally, which can help flare the anchor 20. Pulling the obturator 18 in a proximal direction also proximally moves the clips 60 attached to the anchor's distal rim 58. The clips' protrusions 60p can have a slanted, tapered, or beveled surface 60s such that a surface of the proximal rim 56 can urge the clips' protrusions 60p radially inwards until the protrusions 60p reach the groove 62 formed in the proximal rim 56. The protrusions 60p can then move radially outward and snap into the groove 62, thereby locking the anchor 20 in the second configuration with the anchor 20 deployed, as illustrated in FIGS. 8 and 9. The obturator 18 can be removed from the device 10 by rotating the obturator 18 about the obturator's longitudinal axis A2 and the working channel's longitudinal axis A to laterally move the bayonet pins 48 within the slots 50 until the bayonet pins 48 axially align with the vertically-extending portion of the slots 50, at which point the obturator 18 can be pulled proximally to disengage the bayonet pins 48 from the slots 50 and allow removal of the obturator 18 from the device 10.

The anchor 20 can also be configured to move from the second configuration with the anchor 20 in a deployed position to the first configuration with the anchor 20 in an undeployed position. In an exemplary embodiment, illustrated in FIG. 10, a release tool 64 can be configured to be inserted into the device's working channel 16 and move the anchor 20 from the second configuration to the first configuration. The release tool 64 is shown as having an elongate shaft with a wedge at a distal end thereof, but the release tool 64 can have a variety of sizes, shapes, and configurations. In use, the release tool 64 can be moved in a distal direction until a distal end of the release tool 64 engages the anchor's pins 60. The release tool's distal end can be in the form of a wedge, e.g., a cylindrical member having a slanted, tapered, or beveled edge 66, configured to slidably engage the slanted, tapered, or beveled surface 60s of the clips 60 and move the clips' protrusions 60p radially inward and distally such that the clips 60 can disengage from the groove 62, thereby allowing the anchor 20 to move to the first configuration.

Figure 11:
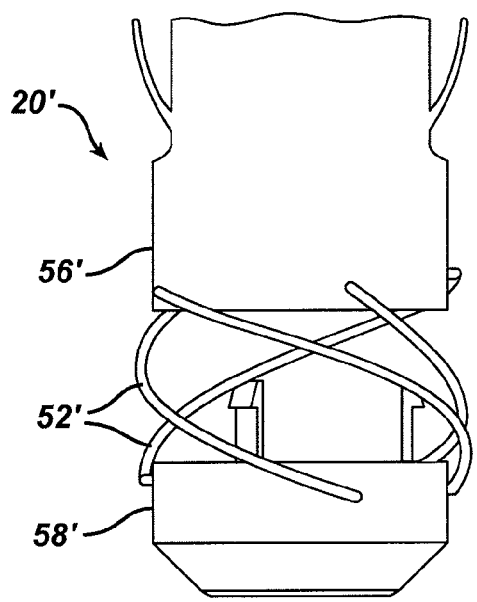
FIG. 11 is a side view of another embodiment of an anchor including a plurality of spiraling flexible wires, the anchor being in an undeployed configuration.
Figure 12:
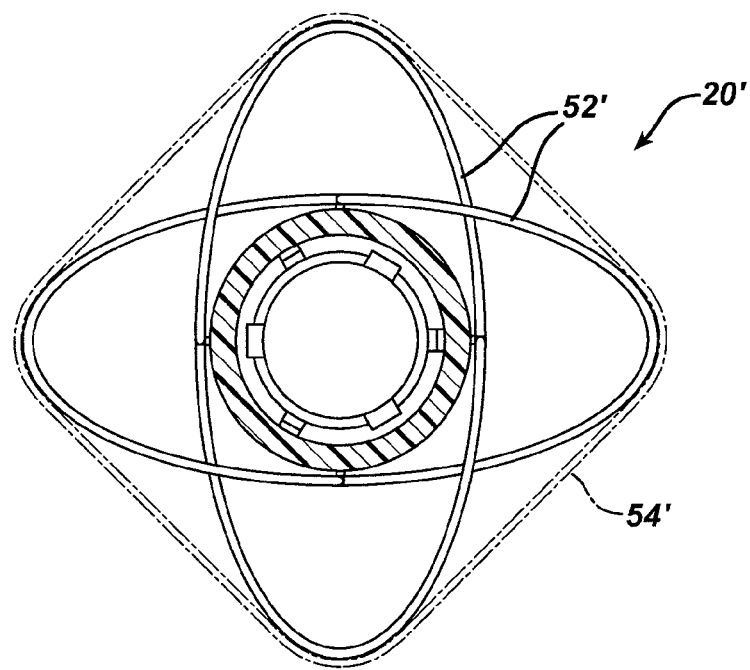
FIG. 12 is a top view of the anchor of FIG. 11 with the anchor in a deployed configuration.
Figure 13:
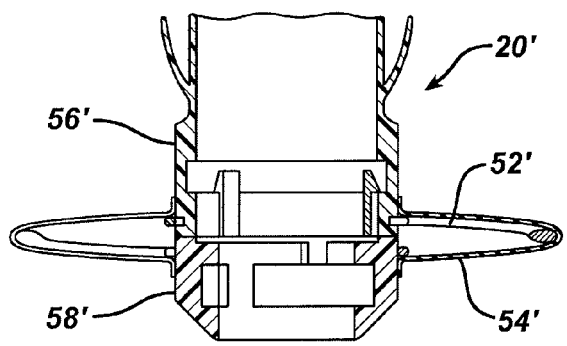
FIG. 13 is a side cross-sectional view of the anchor of FIG. 12.

FIGS. 11-13 illustrate another exemplary embodiment of an anchor 20' including a plurality of flexible wires 52' extending between proximal and distal rims 56', 58' of the anchor 20'. A flexible outer sheath 54', not shown in FIG. 11 for clarity, can be disposed around the wires 52'. The anchor 20' can generally be configured and used similar to the anchor 20 of FIGS. 1, 2, and 7-10. However, in this illustrated embodiment, instead of extending substantially parallel to a longitudinal axis A' of the anchor 20' when the anchor 20' is undeployed, e.g., in a first configuration shown in FIG. 11, the wires 52' can spiral between the proximal and distal rims 56', 58'. When deployed, e.g., in a second configuration shown in FIGS. 12 and 13, the spiraled wires 52' can allow a greater surface area of the wires 52' to abut and grip tissue, with the sheath 54' optionally positioned therebetween, than with longitudinal wires.

Figure 14:
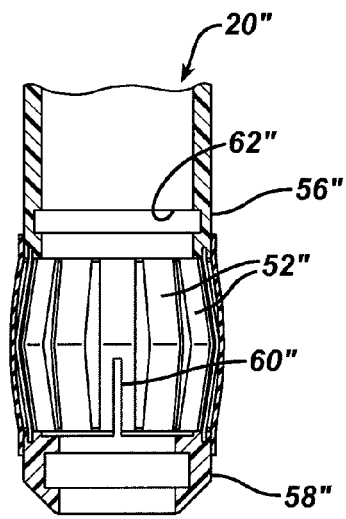
FIG. 14 is a side cross-sectional view of another embodiment of an anchor including a plurality of wide flexible wires, the anchor being in an undeployed configuration.
Figure 15:
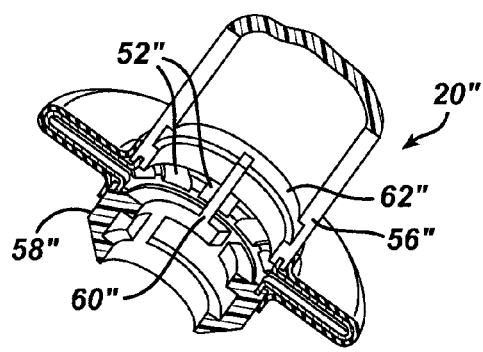
FIG. 15 is a perspective cross-sectional view of the anchor of FIG. 14 in a deployed configuration.
Figure 16:
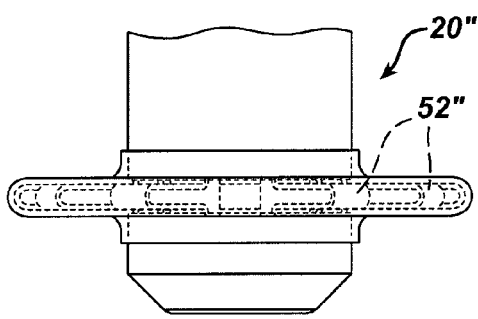
FIG. 16 is a side, partially transparent view of the anchor of FIG. 15.
Figure 17:
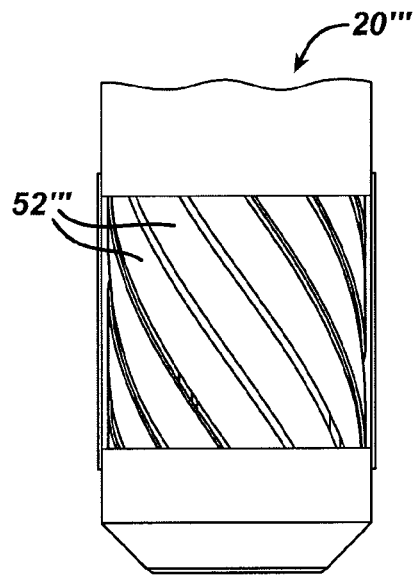
FIG. 17 is a side, partial cross-sectional view of another embodiment of an anchor including a plurality of spiraling wide flexible wires, the anchor being in an undeployed configuration.
Figure 18:
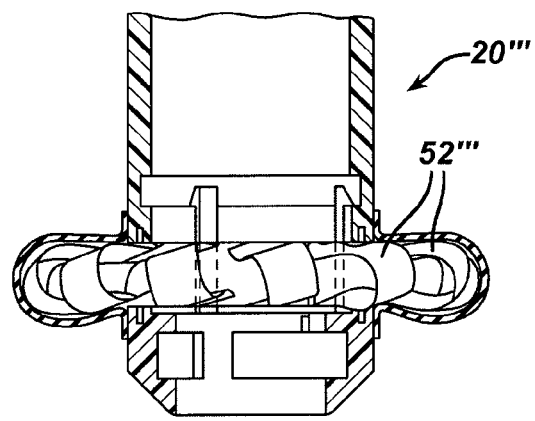
FIG. 18 is a side cross-sectional view of the anchor of FIG. 17 with the anchor in a deployed configuration.

The wires 52, 52' discussed above include thin, rod-like members, but in another exemplary embodiment, an anchor can include a plurality of flexible wide, planar wires. Such wide, planar wires can be configured and used similar to the wires 52, 52' discussed above but can allow a greater surface area of the wires to abut tissue, with a sheath optionally positioned therebetween, than with thin, rod-like members. FIGS. 14-16 illustrate one exemplary embodiment of an anchor 20" including a plurality of flexible wide, planar wires 52" extending substantially parallel to a longitudinal axis A" of the anchor 20" between proximal and distal rims 56", 58" of the anchor 20". When the anchor 20" is deployed, the wires 52" can bend as shown in FIGS. 15 and 16 to increase a diameter of the anchor 20", with a plurality of posts 60" extending from the distal rim 58" engaging a groove 62" formed in the proximal rim 56" to at least temporarily lock the anchor 20" in the deployed position. FIGS. 17 and 18 illustrate another exemplary embodiment of an anchor 20''' including a plurality of flexible wide, planar wires 52''' that spiral between proximal and distal rims 56''', 58''' of the anchor 52'''.

Figure 19:
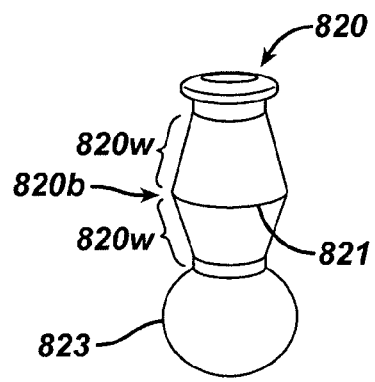
FIG. 19 is a perspective view of another embodiment of an anchor including a distal bead and a bellows, the anchor being in an undeployed configuration.
Figure 20:
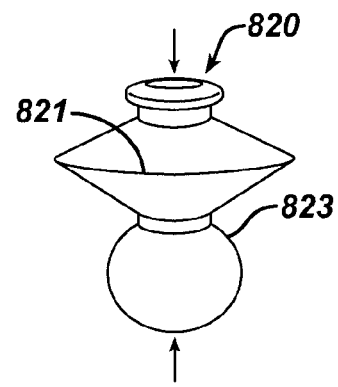
FIG. 20 is a perspective view of the anchor of FIG. 19 with the anchor in a deployed configuration.

The anchors 20, 20', 20" can each freely collapse when moving from the first configuration to the second configuration. In other exemplary embodiments, an anchor can be configured to bend in at least one predefined bending region when moving from the first configuration to the second configuration. Having a predefined bending region can help maximize a surface area of the anchor that contacts tissue when the anchor is deployed. FIGS. 19 and 20 illustrate one exemplary embodiment of an accordion-type anchor 820 having a predefined bending region 820b located between two adjacent accordion waves 820w of the anchor 820. When the anchor 820 moves from a first, undeployed configuration, shown in FIG. 19, to a second, deployed configuration, shown in FIG. 20, the anchor 820 can be configured to bend at the predefined bending region 820b. The predefined bending region 820b can have a variety of configurations, such as being a scored or otherwise weakened portion of the anchor 820. In the illustrated embodiment, a ring 821 can be positioned between the accordion waves 820w around an exterior surface of the anchor 820, within the anchor 820, and/or inside an interior surface of the anchor 820. The ring 821 can have a c-shape as shown or can have another shape, e.g., an o-shape. The ring 821 can be made from any one or more materials, such as a shape memory material, e.g., Nitinol, spring steel, etc. The ring 821 can be configured to facilitate deployment of the anchor 820 and engagement of the anchor 820 with tissue by increasing a force of the anchor's collapse, e.g., by being biased to an enlarged ring shape, and by urging the anchor 820 to a predefined diameter in the second configuration that is larger than the anchor's diameter in the first configuration. The anchor 820 can optionally include a distal retention bead 823 as its distal rim at a distal-most end of the anchor 820. The retention bead 823 can have a variety of sizes, shapes, and configurations, e.g., a sphere.

Figure 21:
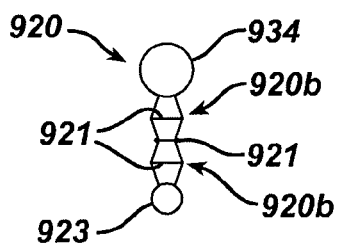
FIG. 21 is a side view of another embodiment of an anchor including a distal bead and an elongated bellows, the anchor being in an undeployed configuration and having its proximal end coupled to a segment of a cannula.

FIG. 21 illustrates another embodiment of an accordion-type anchor 920 having multiple accordion waves 920w each having a predefined bending region 920b in a mid-portion thereof. A c-ring 921 can be positioned at the predefined bending regions 920b and/or between the accordion waves 920w around an exterior surface of the anchor 920, within the anchor 920, and/or inside an interior surface of the anchor 920. The anchor 920 in FIG. 21 is illustrated with a distal retention bead 923 and as coupled at its proximal end to a spherical segment 934.

As mentioned above, a surgical access device can include a cannula having a plurality of biased segments such that the cannula can be configured to dynamically adjust its longitudinal length. In some exemplary embodiments, a surgical access device can include a cannula configured to have an adjustable longitudinal length, but the cannula can be formed of a continuous elongate tubular member rather than a plurality of independent segments coupled together to form a tubular member. In one exemplary embodiment, a housing can be configured to rotate relative to a cannula distally extending therefrom and cut a proximal end of the cannula to adjust the cannula's longitudinal length. Exemplary embodiments of rotatable housings configured to trim a cannula attached thereto are described in more detail in U.S. patent application Ser. No. 12/636,205 entitled "Methods And Devices For Providing Access Through Tissue To A Surgical Site," filed Dec. 11, 2009, and in U.S. patent application Ser. No. 12/636,232 entitled "Methods And Devices For Providing Access Through Tissue To A Surgical Site," filed Dec. 11, 2009, which are hereby incorporated by reference in their entireties.

Figure 22:
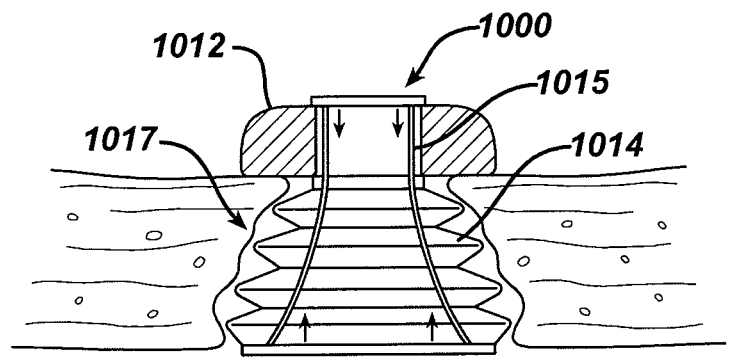
FIG. 22 is a side cross-sectional view of one embodiment of a surgical access device including a cannula formed of a flexible bellows and having a conical elastic component disposed in the cannula, the surgical access device being positioned in an opening in tissue.
Figure 23:
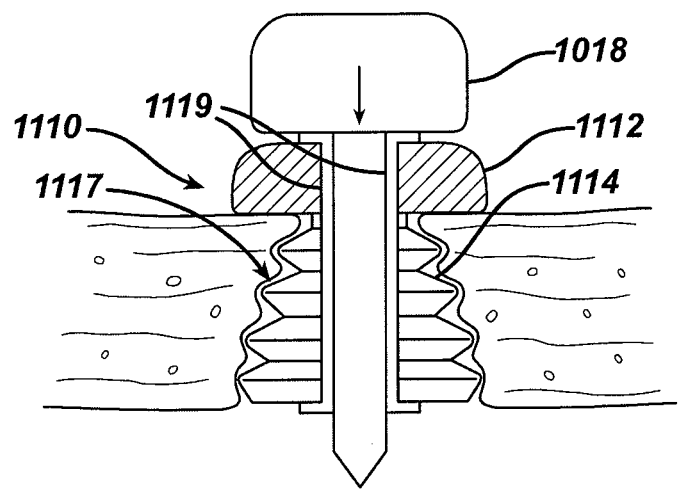
FIG. 23 is a side cross-sectional view of another embodiment of a surgical access device including a cannula formed of a flexible bellows and having an obturator disposed through the cannula and inserting stay clips within the cannula, the surgical access device being positioned in an opening in tissue.
Figure 24:
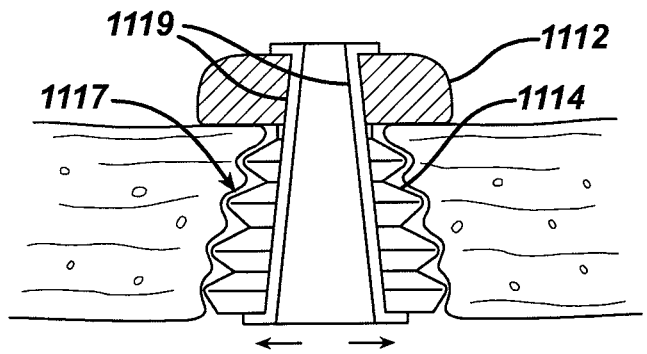
FIG. 24 is a side cross-sectional view of the surgical access device of FIG. 23 with the stay clips deployed in the cannula and with the obturator removed from the surgical access device.

In another exemplary embodiment, illustrated in FIG. 22, including a continuous elongate tubular cannula, a surgical access device 1000 can include a housing 1012 having a cannula 1014 in the form of a bellows extending distally therefrom. The cannula 1014 can optionally include a conical elastic component 1015 and/or a molded-in helical coil (not shown) configured to facilitate expansion and collapse of the cannula 1014 such that the cannula 1014 can change in longitudinal length and be securely positioned within a tissue opening 1017. FIGS. 23 and 24 illustrate another exemplary embodiment of a surgical access device 1100 including a housing 1112 having a cannula 1114 in the form of a bellows extending distally therefrom. An obturator 1118 can be configured to deploy at least one stay clip 1119, e.g., two spring stock clips, within the cannula 1114, as shown in FIG. 23. The stay clips 1119 can be configured to remain inside the cannula 1114 when the obturator 1118 is removed therefrom, as shown in FIG. 24, to exert a radially-outward force to aid retention of the cannula 1114 within a tissue opening 1117.

In some exemplary embodiments, a surgical access device can be configured to have a selectively adjustable longitudinal length using a manipulable adjustment mechanism. Such a surgical access device can include a plurality of segments, or the device's cannula can be otherwise configured to be flexible as a continuous elongate tubular member.

Figure 25:
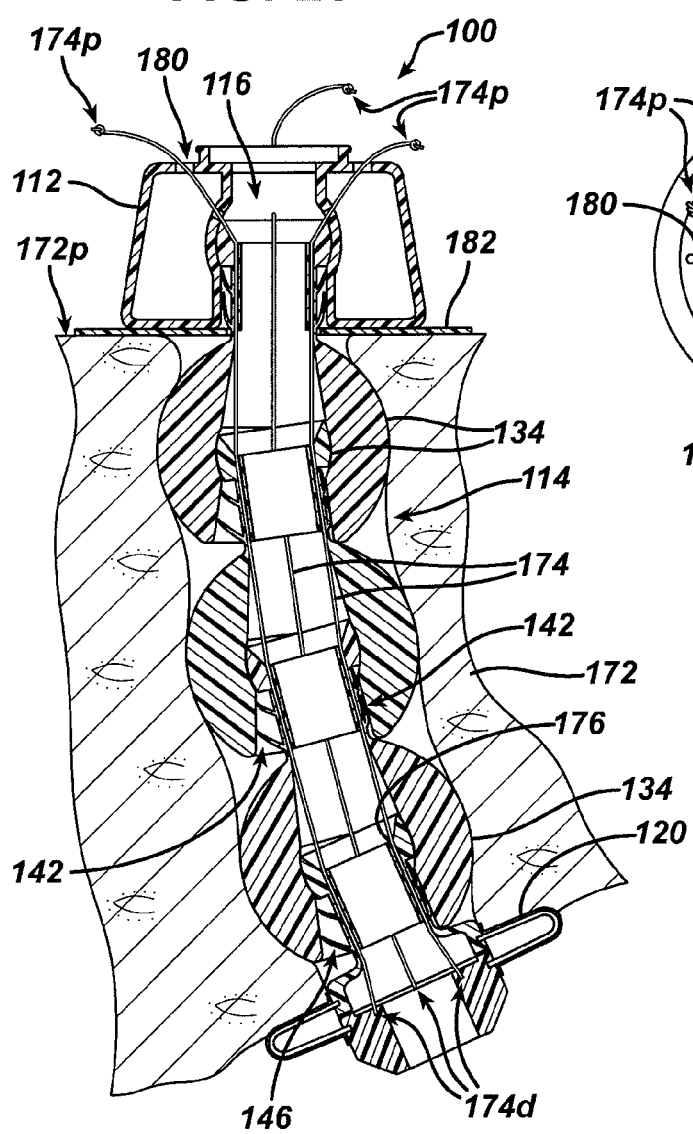
FIG. 25 is a side cross-sectional view of one embodiment of a surgical access device positioned within an opening in tissue and having a housing with a cannula distally extending therefrom, the cannula including a plurality of segments movably coupled to one another and having an anchor in a deployed configuration at a distal end thereof, the surgical access device including a plurality of pull strings configured to move the segments relative to one another and to move the anchor between deployed and undeployed configurations.
Figure 26:
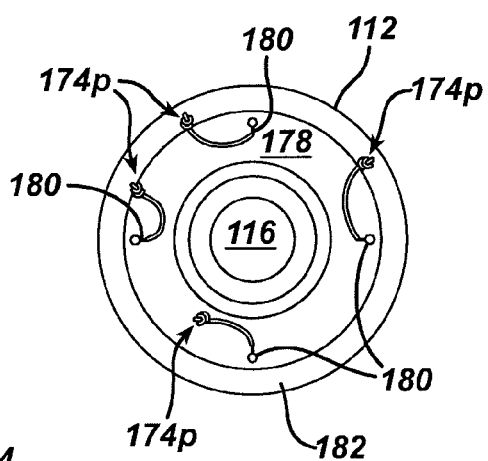
FIG. 26 is a top view of the surgical access device of FIG. 25.

FIGS. 25 and 26 illustrate an exemplary embodiment of a surgical access device 100 that can generally be configured and used similar to the surgical access devices described above but that can have its longitudinal length selectively adjusted using a manipulable adjustment mechanism in the form of a plurality of pull cables, pull strings, pull threads, pull bands, pull ribbons, pull strips, or pull wires 174, generally referred to as "pull strings," spaced longitudinally apart from one another and extending along a longitudinal length of the device 100. The device 100 can also include a distal platform or seal 182, as can any of the devices described herein, configured to abut a proximal surface 172p of tissue 172 in which the device 100 is positioned to help provide a seal and facilitate nonslidable gripping the tissue 172. As illustrated, the device 100 can include a housing 112 and a cannula 114 distally extending therefrom. The cannula 114 can include a plurality of segments 134 and an anchor 120 at a distal end thereof, and can optionally have a protective sleeve disposed therearound.

Although the device 100 is illustrated as having four pull strings 174, a surgical access device can include one or more pull strings, which can have a variety of sizes, shapes, and configurations. Each of the pull strings 174 can have a first, distal terminal end 134d connected to the anchor 120 and a second, proximal terminal end 134p extending proximally beyond the housing 112 such that the second terminal end 134p can be manipulated outside tissue 172. A longitudinal length of each pull string 174 extending between the terminal ends 174d, 174p can pass through lumens 176 within necks of the segments 134 to securely couple the string 174 thereto. Although the anchor 120 can be removable from the device 100 as mentioned above, because the anchor 120 is attached to the pull strings 174 in the illustrated embodiment, the anchor 120 is nonremovable from the device 100 to ease handling of the device 100. Similarly, the segments 134 can be modular as discussed above and as illustrated in FIG. 25 such that any number of segments 134 can be attached together to form the cannula 114.

The pull strings 174 can be configured to be individually manipulated and/or to be manipulated two or more at a time. The pull strings 174 can also be configured to adjust the cannula's longitudinal length and/or to bend the cannula 114. Pulling at least one of the pull strings 174 in a proximal direction can pull the anchor 120 in a proximal direction, thereby compressing the cannula 114 to reduce its longitudinal length. If less than a total number of the pull strings 174 are pulled in a proximal direction, the cannula 114 can bend, similar to motion of a marionette. Flexible biasing elements 142 of the segments 134 and flexible biasing elements 146 of the anchor 120 can flex as discussed above to allow movement of the segments 134 and the anchor 120 relative to one another to adjust the cannula's longitudinal length and/or the cannula's curvature.

The device 100 can include a locking mechanism configured to lock the pull strings 174 in position to hold the cannula 114 in a desired configuration. The locking mechanism can have a variety of sizes, shapes, and configurations. In the illustrated embodiment, the locking mechanism includes a plurality of key holes 180 formed in a proximal surface 178 of the housing 112. Each of the key holes 180 can be configured to receive one of the pull strings 174 and to selectively allow and prevent free passage of its associated pull string 174. Although a number of key holes 180 in the illustrated embodiment equals a number of pull strings 174, any one or more of the key holes 180 can be configured to receive and lock two or more pull strings 174 such that the device 100 includes fewer key holes 180 than pull strings 174. The key holes 180 each include an opening formed in the housing's proximal surface having a wide portion and a narrow portion, although they can have a variety of sizes, shapes, and configurations. The wide portion can have a diameter wider than a diameter of its associated pull string 174 to allow free slidable movement of a pull string therein, while the narrow portion can have a diameter narrower than the diameter of its associated pull string 174 to lock the pull string 174 in position therein. Each of the proximal terminal ends 174p of the pull strings 174 can have a diameter larger than its associated key hole wide portion's diameter, e.g., by being knotted, including an end cap, including an aglet, etc. In this way, the pull strings 174 can be prevented from slipping through the key holes 180 and into a working channel 116 of the device 100 where they cannot be as easily manipulated.

FIG. 27 illustrates a sleeve 170 disposed around the cannula 114 of FIG. 25. The sleeve 170 can have a variety of sizes, shapes, and configurations, but can as shown include a fluid-impermeable flexible member disposed over an external surface of the cannula 114 to facilitate sealing of the cannula 114 and facilitate insertion and removal of the cannula 114 from tissue. The sleeve 170 in the illustrated embodiment is adhered to external surfaces of each of the segments 134 using a glue or other adhesive, but as will be appreciated by a person skilled in the art, the sleeve 170 can be attached to the cannula 114 in any number of ways, e.g., through a tight cling fit. The sleeve 170 can optionally be positioned within a tissue opening separately from the cannula 114, and the cannula 114 can be inserted into sleeve 170 already positioned in the tissue opening. A proximal portion of the sleeve 170 can be trimmed to reflect removal of any segments 134 from a proximal end of the cannula 114 and reduce chances of the sleeve 170 interfering with the housing 112 and/or the surgical work space. The sleeve 170 can be a continuous member extending along the cannula 114, as shown in FIG. 27, or the sleeve 170 can include a plurality of discrete members.

Figure 29:
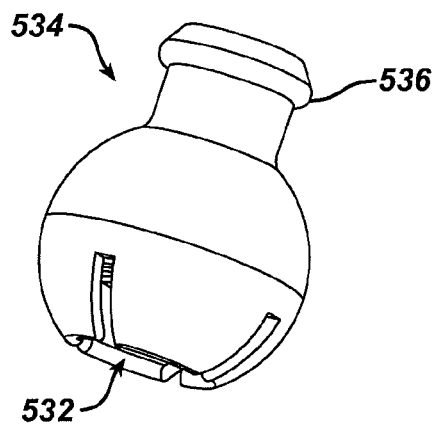
FIG. 29 is a perspective view of one of the segments of FIG. 28.

FIGS. 28 and 29 illustrate one exemplary embodiment of a surgical access device 500 including a housing 512 with a cannula 514 distally extending therefrom and having a protective sleeve formed of a plurality of discrete members 570 disposed therearound. The device 500 can be configured and used similar to the device 100 and can have an adjustable longitudinal length. A surgical instrument 519 is shown in FIG. 28 disposed through a working channel 516 defined by the housing 512 and the cannula 514.

The sleeve members 570 forming the sleeve can have a variety of sizes, shapes, and configurations and can be attached to the cannula 514 in any way. In the illustrated embodiment, the sleeve members 570 are configured as tape and include elongate strips coupled together using an adhesive such as biocompatible glue. Each of the sleeve members 570 can be adhered to at least one adjacent sleeve member 570 such that the sleeve members 570 overlap to collectively form a continuous sleeve.

The cannula 514 can include a plurality of removably and pivotably coupled segments 534 connected together by snap fit with an anchor 520 removably and pivotably connected by snap fit to a distal-most one of the segments 534. Thus, the device's longitudinal length can be adjusted by selectively removing and adding segments 534 to the cannula 520. The segments 534 can include mating features, e.g., male and female members 536, 532, configured to allow the adjacent segments to pivot relative to one another to allow the cannula 514 to bend, as shown in FIG. 28. Each of the segments 534 can include at least one slot 537 extending proximally from a distal end of the segment 534 along a partial longitudinal length of the segment 534. The segments 534 each include four slots, but the segments 534 can include any number of slots 537. The slots 537 can facilitate bending of the cannula 514 when a male member 536 of one of the segments 534 pivots within the female member 532 of an adjacent segment 534. Because the segments 534 have the slots 537 formed through sidewalls thereof, the segments 534 in the illustrated embodiment are not connected together with a fluid-tight seal. The sleeve disposed around the cannula 514 can thus be configured to provide a fluid-tight seal of the cannula 514.

Figure 30:
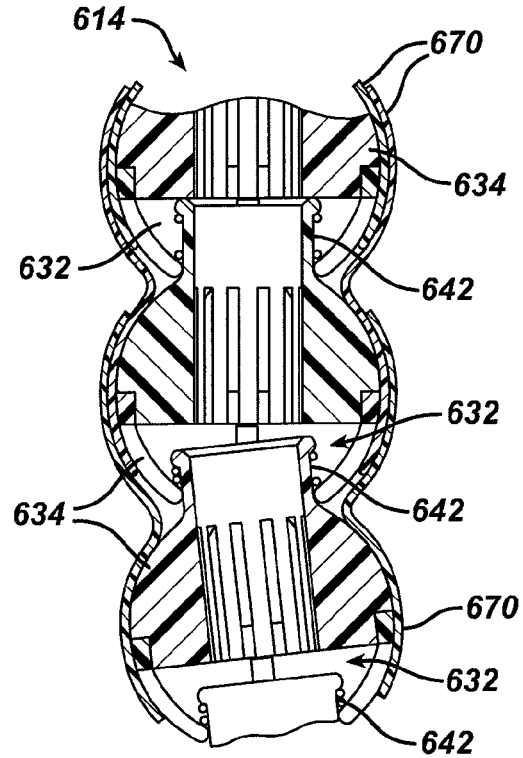
FIG. 30 is a side cross-sectional view of another embodiment of a cannula including a plurality of segments movably coupled to one another, the segments each including a biasing spring.
Figure 31:
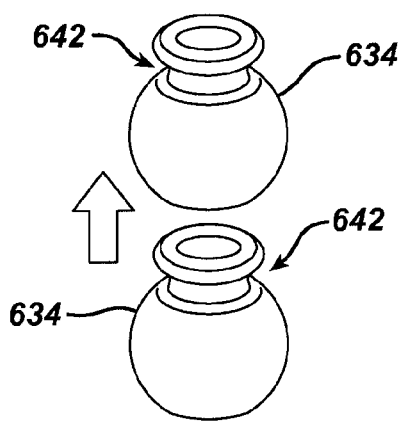
FIG. 31 is a perspective view of segments of FIG. 30.

FIG. 30 illustrates another embodiment of a cannula 614 including a plurality of segments 634 coupled together by snap fit and having a continuous sleeve disposed therearound and formed from a plurality of discrete sleeve members 670. The cannula 614 and the sleeve members 670 can be configured and used similar to the cannula 514 and the sleeve members 570 of FIGS. 28 and 29 discussed above, but the segments 634 in the embodiment of FIG. 30, also illustrated in FIG. 31 as independent elements, include flexible biasing elements 642 configured to allow adjustment of the cannula's longitudinal length. The biasing elements 642 can be configured and used similar to the biasing elements 42 of FIG. 2 discussed above. In the illustrated embodiment, the biasing elements 642 include compressible coils or springs biased to a default, compressed configuration to thereby bias the cannula 614 to a compressed configuration. The biasing elements 642 can, as shown in FIGS. 30 and 31, be coiled around an external surface of necks of their respective segments 634 and be configured to be contained within a female member 632 of an adjacent segment 634.

Figure 32:
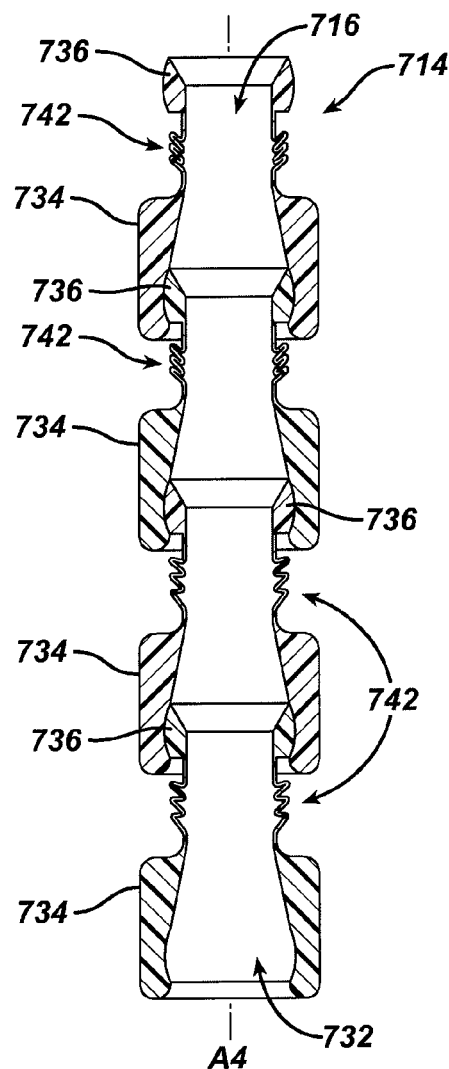
FIG. 32 is a side cross-sectional view of one embodiment of a cannula including a plurality of segments movably and removably coupled to one another, the segments each including a flexion region.
Figure 33:
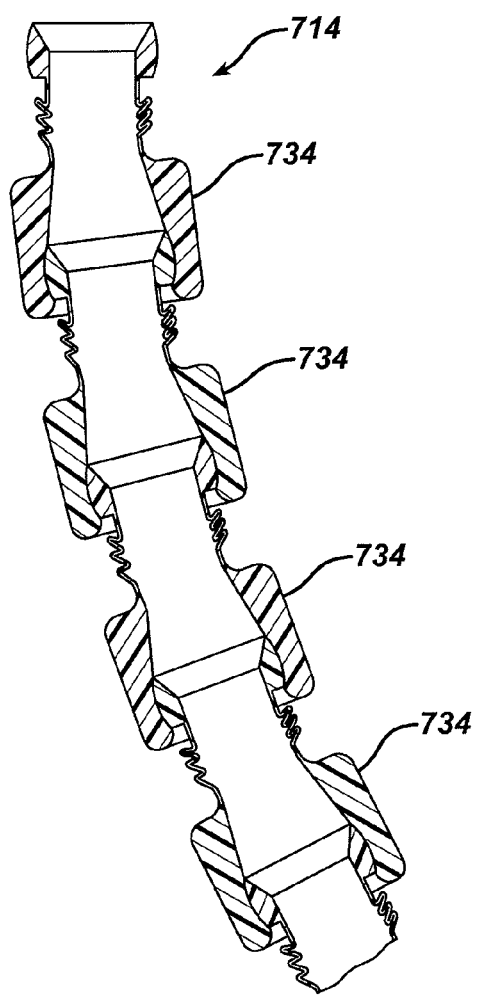
FIG. 33 is a side cross-sectional view of the cannula of FIG. 32 with the cannula in a curved position.

In another exemplary embodiment, a segment's biasing element can be disposed outside an adjacent segment rather than being contained within the adjacent segment's distal cavity as in the embodiments illustrated in FIGS. 2 and 30. In one exemplary embodiment illustrated in FIGS. 32 and 33, a cannula 714 can include a plurality of segments 734 movably coupled together that can be configured and used similar to the segments 34 of FIG. 2. However, the segments 734 of FIGS. 32 and 33 each have a flexion region 742 such that the segments 734, when coupled together to form the cannula 714, can be movable toward and away from one another along a longitudinal axis A4 of the cannula's working channel 716 to allow a length of the cannula 714 to be adjusted. The flexion regions 742 can have a variety of sizes, shapes, and configurations, e.g., a bellows (as shown in FIGS. 32 and 33), nested folds, a weakened region, etc., and can generally be configured to expand and compress upon application of a force, e.g., when curved through tissue, when an obturator coupled to an anchor (not shown) coupled to a distal-most one of the segments 734 is manipulated as discussed above, etc. Because the flexion regions 742 can be configured to be flex to allow the cannula 714 to bend and to adjust in length, and because the flexion regions 742 can be disposed outside adjacent segments 734 when the segments 734 are coupled together, male members 736 configured to be received in female members 732 of adjacent segments 734 can be non-movably and/or non-removably seated therein, which can help provide a fluid-tight seal between adjacent segments 734 such that the working channel 716 can be fluid tight.

Figure 34:
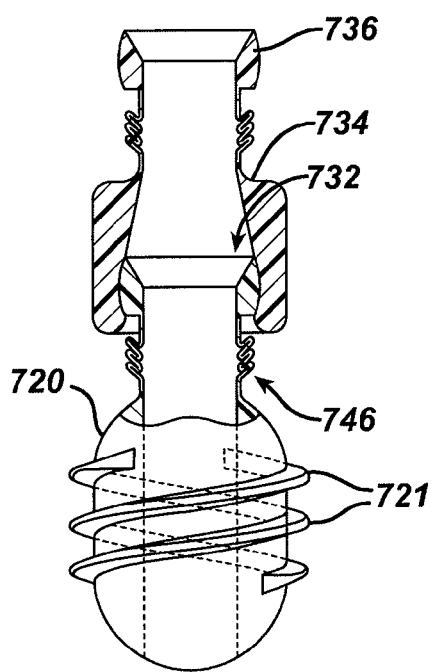
FIG. 34 is a side, partial cross-sectional, partially transparent view of an anchor movably and removably coupled to one of the segments of FIG. 32, the anchor having a plurality of threads formed thereon.
Figure 35:
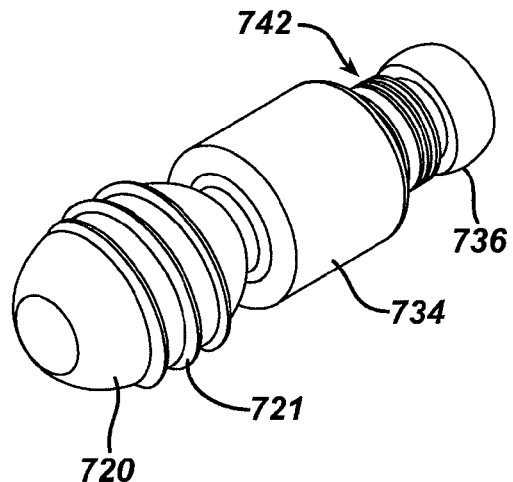
FIG. 35 is a perspective view of the segment and the anchor of FIG. 35.

Optionally, an anchor can be coupled to a distal-most one of the segments 734. FIGS. 34 and 35 illustrate an exemplary embodiment of an anchor 720 having a bulb shape and being configured to be coupled to the distal-most one of the segments 734. However, as mentioned above and as will be appreciated by a person skilled in the art, any of the anchors discussed herein, including the anchor 720, can be configured to couple to any cannula described herein. The anchor 720 can be configured and used similar to the anchor 20 of FIGS. 1 and 2, but the anchor 720 in the illustrated embodiment includes a flexion region 746 (obscured in FIG. 35) similar to the flexion regions 742 of the segments 734. The anchor 720 can also include at least one thread 721, e.g., two threads as illustrated in FIGS. 34 and 35, spiraling around an exterior surface thereof The threads 721 can have a variety of sizes, shapes, and configurations, as will be appreciated by a person skilled in the art. The threads 721 can be configured to engage tissue and facilitate insertion and retention of the anchor 720 therein. The anchor 720 can thus be configured to be at least partially disposed within tissue to attach a surgical access device including the anchor 720 to the tissue.

In use, the anchor 720 can be inserted through an opening in tissue until the anchor 720 is positioned within a body cavity underlying the tissue. Then, the anchor 720 can be moved proximally and rotated about its longitudinal axis to engage tissue distally facing the body cavity to dispose and retain the anchor 720 at least partially therein.

FIGS. 36-38 illustrate one exemplary embodiment of a deployment system that can be configured to position the cannula 714 within a tissue opening and to deploy the anchor 720 at the cannula's distal end. Similar to that discussed above regarding the obturator 18 and the device 10 of FIG. 1, an obturator 718 can be configured to be slidably disposed through the cannula's working channel 716 with a proximal handle 728 of the obturator 718 being located proximal to a proximal end of the cannula 714 and with a distal tip 730 of the obturator 718 extending distally beyond the anchor 720, as shown in FIG. 37. The obturator's handle 728 can have a maximum diameter 728*d* greater than the working channel's diameter 718*d* at the working channel's proximal end to prevent the obturator 718 from being fully inserted into the cannula 714 through a proximal end thereof such that the obturator 718 cannot be easily manipulated from outside a patient's body. The obturator 718 can be configured as a bladed trocar such that obturator's distal tip 730 can include at least one slot 730*s*, e.g., four slots, formed through a sidewall thereof and extending proximally from a distal-most end of the obturator 718. If the obturator 718 includes a plurality of slots 730*s* as in the illustrated embodiment, the slots 730*s* can define a plurality of fingers 730*g* that form the distal tip 730. The slots 730*s* can be configured to allow radial expansion of the obturator's distal tip 730 in an outward direction. The obturator 718 can be hollow and have an inner lumen 719 extending therethrough. The inner lumen 719 can be configured to slidably receive a surgical instrument, such as an expander tool 731. At least a portion of the inner lumen 719, e.g., within the handle 728, can be threaded (not shown) to engage corresponding threads (not shown) on the expander 731.

The expander 731 can include a proximal handle 723 having a maximum diameter 723*d* greater than a diameter 719*d* of the obturator's inner lumen 719 at the inner lumen's proximal end to prevent the expander 731 from passing into the obturator 718 through a proximal end thereof such that the expander 731 cannot be easily manipulated. The expander 731 can include a tapered or conical distal tip 725. The expander 731 can be configured to be slidably inserted into the obturator's inner lumen 719 such that the expander's distal tip 725 can be disposed at least partially within the obturator's distal tip 730 to radially expand the obturator's distal tip 730, as shown in FIG. 38. When the obturator's distal tip 730 is positioned within the anchor 720 such that at least a portion of the slots 730 and the fingers 730g are positioned therein, and when the obturator 718 with the expander 731 positioned therein such that the expander's distal tip 725 radially expands the obturator's distal tip 730, as also shown in FIG. 38, outer surfaces of the obturator's fingers 730g can grip an inner surface of the working channel 716 within the anchor 720 to thereby form a compression lock between the obturator 718 and the anchor 720. The anchor 720 can be configured to substantially not expand when the obturator's distal tip 730 expands, e.g., by being formed of a substantially rigid material and/or including a substantially rigid lining on its inner surface facing the working channel 716.

Locked to the anchor 720, the obturator 718 can be rotated, e.g., by rotating the handle 728, about a longitudinal axis of the obturator 718 relative to the segments 734 of the cannula 714, and, if present, to a housing (not shown) at a proximal end of the cannula 714, to thereby rotate the anchor 720. A mating feature of the anchor 720, e.g., a male member 740, can be configured to be rotatably seated within a mating feature, e.g., 738, of the distal-most segment 734 to allow the anchor 720 to be rotated relative thereto. With the anchor 720 being disposed in a body cavity, rotating the anchor 720 in a proximal direction can rotate the anchor 720 into tissue to thereby secure the anchor 720 therein. As mentioned above, the anchor's threads 721 can be configured to help grip the tissue and securely hold the anchor 720 therein. The anchor 720 can be rotated any depth into the tissue, with the threads 721 entirely or partially engaging the tissue. In an exemplary embodiment, at least a distal-most end of the anchor 720 can remain disposed in the body cavity when the anchor 720 is threaded into the tissue.

When the anchor 720 is threaded into tissue, the expander 731 can be removed from the obturator's distal tip 730 such that the distal tip 730 can radially collapse to release the compression lock between the anchor 720 and the obturator 718. The expander 731 and the obturator 718 can then be removed separately or together from the working channel 716 such that the working channel 716 can provide a pathway through tissue.

The anchor 720 can be removed from the tissue in a similar way to its disposal therein. The obturator 718 can be slidably disposed within the working channel 716, and the expander 731 can be disposed within the obturator's inner lumen 719 and radially expand the obturator's distal tip 730 to form a compression lock between the anchor 720 and the obturator 718. Rotating the obturator 718 can correspondingly rotate the anchor 720 to rotate the anchor 720 out of the tissue. The obturator 718, the expander 731, and the anchor 720 can then separately or together be removed from the patient's body.

Figure 39:
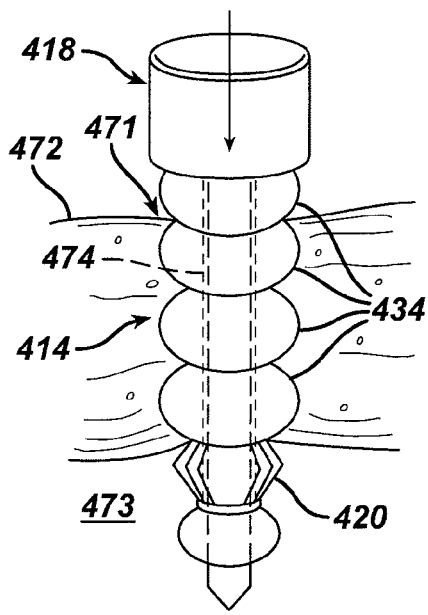
FIG. 39 is a side partial cross-sectional view of one embodiment of a surgical access device positioned within an opening in tissue, including a plurality of movably and removably coupled segments with an anchor at a distal end thereof in an undeployed configuration, and having a surgical instrument inserted through a working channel of the surgical access device, the surgical access device including a plurality of pull strings configured to move the segments relative to one another and to move the anchor between deployed and undeployed configurations.
Figure 40:
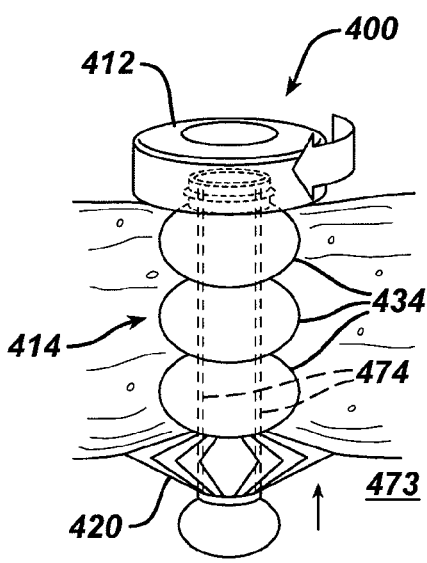
FIG. 40 is a side partial cross-sectional view of the surgical access device of FIG. 39 with a housing removably attached to a proximal-most one of the segments, the anchor being in a deployed configuration.

FIGS. 39 and 40 illustrate another exemplary embodiment of a surgical access device 400 including a manipulable adjustment mechanism in the form of a plurality of pull strings 474 configured to selectively adjust a longitudinal length of the device's cannula 414. As shown, the cannula 414 can be formed of a plurality of modular segments 434 and have an anchor 420 at a distal end thereof. In use, as shown in FIG. 39, an obturator 418 can be disposed in an inner lumen of the cannula 414, and the cannula 414 with the obturator 418 disposed therethrough can be positioned in an opening 471 in tissue 472 such that at least the anchor 420 is positioned in a body cavity 473 underlying the tissue 472. The obturator 418 can then be removed from the cannula 414, and one or more excess segments 434, one in the illustrated embodiment, can be removed, e.g., unsnapped, from a proximal end of the cannula 414, to reduce a longitudinal length of the cannula 414 as shown in FIG. 40. The pull strings 474 extending through the cannula 414 and being connected to the anchor 420 can also be pulled in a proximal direction to further reduce the cannula's length by deploying the anchor 420 from a first configuration, shown in FIG. 39, to a second configuration, shown in FIG. 40.

Either before or after the anchor 420 is deployed, a housing 412 can be attached to a proximal-most one of the segments 434 at a proximal end of the cannula 414. The housing 412 can be configured and used similar to the housing 12 discussed above. In this way, the device 400 including the housing 412 and the cannula 414 can be secured within the tissue opening 471 such that one or more surgical instruments can be inserted therethrough to access the body cavity 473.

In addition or in alternative to the pull strings being individually or collectively pullable, the housing can be configured to rotate about a longitudinal axis of the device to move the pull strings. In this way, compression of tissue between the housing and the distal anchor can be adjusted any number of times during a surgical procedure to desirably secure the surgical access device within an opening in the tissue. Rotating the housing in a first direction, e.g., clockwise, can move the pull strings in a proximal direction to shorten the cannula, and rotating the housing in a second direction, e.g., counter-clockwise, can move the pull strings in a distal direction to lengthen the cannula. The housing can slidably move relative to the distal platform or seal.

Figure 41:
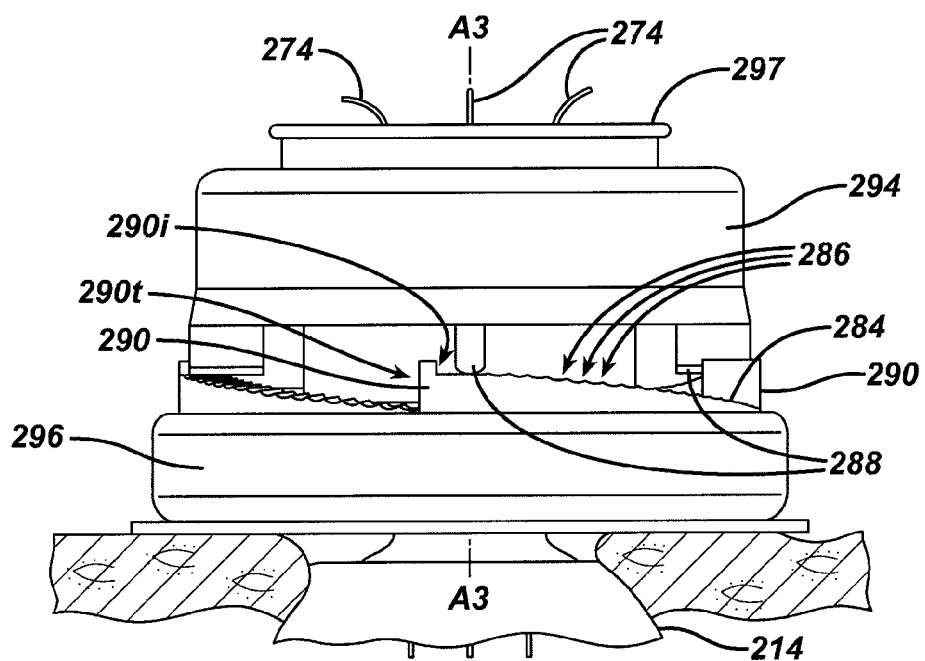
FIG. 41 is a side partial cross-sectional view of one embodiment of a surgical access device positioned within an opening in tissue and including a rotatable housing having a cannula formed of a plurality of movably and removably coupled segments extending distally therefrom, the surgical access device including a plurality of pull strings configured to move the segments relative to one another when the housing rotates.
Figure 42:
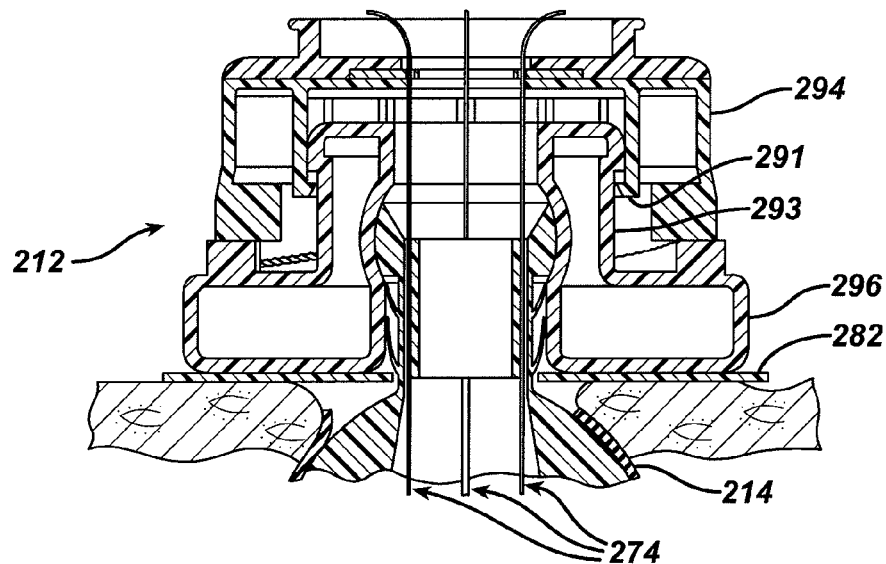
FIG. 42 is a side cross-sectional view of the surgical access device of FIG. 41.
Figure 43:
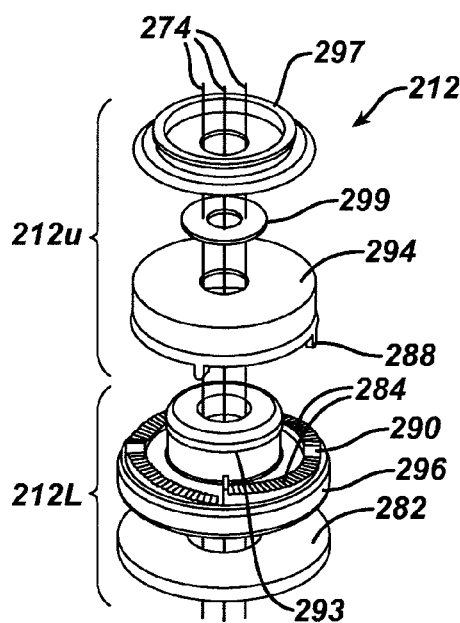
FIG. 43 is an exploded perspective view of the housing and pull strings of FIG. 41.

FIGS. 41-43 illustrate an exemplary embodiment of a housing 212 configured to rotate about a longitudinal axis A3 of the housing 212 to move a plurality of pull strings 274 to adjust a longitudinal length and/or curvature of a cannula 214 distally extending from the housing 212. Generally, the housing 212 can include upper and lower portions 212u, 212L with the upper portion 212u being configured to rotate relative to the lower portion 212L to adjust a length of the cannula 214. The upper and lower portions 212u, 212L can have a variety of sizes, shapes, and configurations. As illustrated, the lower portion 212L can include a base ring 296 and a distal platform or seal 282, and the upper portion 212u can include a cap 294, a valve assembly ring 297 coupled to a proximal end of the cap 294 and configured to attach to a proximal housing (not shown), and a retention ring 299 held by interference fit and positioned between the valve assembly ring 297 and the cap 294. The pull strings 294 can extend through holes 295 in the retention ring 299 and be secured therein similar to that described above regarding the narrow portions of the key holes 180 of FIGS. 25 and 26. The pull strings 294 can otherwise extend through central lumens of the base ring 296, the distal platform or seal 282, the cap 294, and the valve assembly ring 297. In this way, rotation of the upper portion 212u of the housing 212 relative to the housing's lower portion 212L and to the cannula 214 can similarly rotate the pull strings 274 relative to the housing's lower portion 212L and the cannula 214 to adjust the cannula's longitudinal length.

The upper and lower portions 212u, 212L of the housing 212 can be rotatably coupled to one another in a variety of ways. As shown, the base ring 296 can include a proximally-extending grip ring post 293 configured to engage a grip ring 291 distally extending from the cap 294. The grip ring 291 can include a continuous circumferential ring as in the illustrated embodiment, or the grip ring 291 can include a plurality of distally extending posts similar to the proximally-extending anchor posts or clips 60 discussed above. The grip ring 291 can be slidably mated to the grip ring post 293 with a radially extending protrusion of the grip ring 291 engaging the grip ring post 293 as shown in FIG. 42.

The base ring 296 can include a plurality of ratchet ramps 284 each having a plurality of detents 286 formed thereon. The cap 294 can include a plurality of distally-extending pawls 288 configured to engage the detents 286 such that rotation of the housing's upper portion 212u about the housing's longitudinal axis A3 relative to the housing's lower portion 296 and to the cannula 214 will cause the pawls 288 to sequentially engage their corresponding teeth 286. Although the housing 212 in the illustrated embodiment includes four ramps 284 and four corresponding pawls 288, a person skilled in the art will appreciate that the housing 212 can include any number of ramps and pawls. Similarly, each of the ramps 284 can slant at any angle and can include any number of detents 286, e.g., twenty detents. The detents 286 can be configured to prevent rotation of a pawl 288 seated within one of the detents 286. In this way, each detent 286 on a ramp 284 can be configured to define an incrementally locked, predetermined position of the housing 212. Each of the predetermined positions can correspond to a longitudinal length of the cannula 214 through which the pull strings 274 longitudinally extend. In other words, when the housing's upper portion 212u is rotated in a first direction, the pawls 288 move proximally or up the slanted ramps 284, the pull strings 274 correspondingly move proximally or up, thereby decreasing a longitudinal length of the cannula 214. Similarly, when the housing's upper portion 212u is rotated in a second, opposite direction, the pawls 288 move distally or down the slanted ramps 284, the pull strings 274 correspondingly move distally or down, thereby increasing a longitudinal length of the cannula 214. In the illustrated embodiment, rotating the housing's upper portion 212u in a clockwise direction shortens the cannula 214, but a person skilled in the art will appreciate that the housing 212 can be configured such that clockwise rotation of the housing's upper portion 212u lengthens the cannula 214.

A proximal-most or highest end of the ramps 284 can each include a stop 290 that has a size configured to prevent further proximal movement of its associated pawl 288, e.g., when the pawl 288 abuts an inner surface 290i of the stop 290. The stops 290 can also each be configured to prevent further distal movement of an adjacent one of the pawls 288, e.g., when the adjacent pawl 288 abuts an outer surface 290t of the stop 290.

When the cannula 294 has been adjusted to a desirable longitudinal length, a proximal housing (not shown but which can be configured and used similar to the housing 12 of FIGS. 1 and 2) including at least one seal element configured to form at least one of an instrument seal and a channel seal can be snapped onto or otherwise attached to the valve assembly ring 297. Excess lengths of the pull strings 274 can optionally be trimmed before attachment of the proximal housing to reduce interference of the pull strings 274 with the proximal housing.

Figure 44:
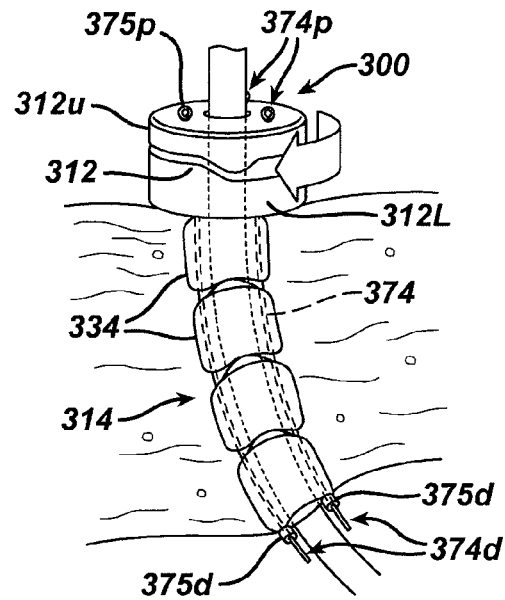
FIG. 44 is a side partial cross-sectional view of another embodiment of a surgical access device positioned within an opening in tissue and including a rotatable housing having a cannula formed of a plurality of movably and removably coupled segments extending distally therefrom, the surgical access device including a plurality of pull strings configured to move the segments relative to one another when the housing rotates.

As mentioned above, a surgical access device need not include a distal anchor, and such a device can include pull strings configured to adjust a longitudinal length of the device's cannula. Rotation of a housing from which the cannula distally extends can be configured to so adjust the cannula's longitudinal length similar to that discussed above regarding FIGS. 41-43. In one exemplary embodiment shown in FIG. 44, a surgical access device 300 includes a housing 312 having upper and lower portions 312u, 312L with a cannula 314 distally extending from the housing 312 and including a plurality of segments 334. Each of the segments 334 in the embodiment shown in FIG. 44 have a cylindrically-shaped distal portion. A plurality of pull strings 374 extending through the housing 312 and the cannula 314 can have proximal terminal ends 374p located proximal to the housing 312 and distal terminal ends 374d located distal to a distal-most one of the segments 374. The terminal ends 374p, 374d are secured in their respective positions using respective aglets 375p, 375d. In this way, the housing's upper portion 312u can be selectively rotated relative to the housing's lower portion 312L and the cannula 314, such that the pull strings 374 can compress the segments 374 to shorten a length of the cannula 314 or relax the segments 374 to lengthen the cannula 314.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a housing, a cannula segment, an anchor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
    a housing having a cannula extending distally therefrom, the housing and the cannula defining a working channel extending therethrough for receiving an instrument, the cannula being movable between an expanded configuration and a compressed configuration, and the cannula including a plurality of segments with a fluid-tight seal formed between adjacent ones of the segments such that the working channel is fluid tight when the cannula is in the expanded configuration and when the cannula is in the compressed configuration, wherein a biasing force biases the cannula to the compressed configuration;
    an adjustment mechanism coupled to the housing and configured to adjust the biasing force; and
    a biasing element coupled to the cannula and configured to apply the biasing force to the cannula:

wherein the biasing element comprises at least one cable extending through the cannula.

2. The surgical access device of claim 1, wherein the adjustment mechanism is configured to adjust a length of the at least one cable to adjust the biasing force.

3. A surgical access device, comprising:
a housing having a cannula extending distally therefrom, the housing and the cannula defining a working channel extending therethrough for receiving an instrument, the cannula being movable between an expanded configuration and a compressed configuration, and the cannula including a plurality of segments with a fluid-tight seal formed between adjacent ones of the segments such that the working channel is fluid tight when the cannula is in the expanded configuration and when the cannula is in the compressed configuration, wherein a biasing force biases the cannula to the compressed configuration; and
an adjustment mechanism coupled to the housing and configured to adjust the biasing force;
wherein the cannula has a length in the expanded configuration that is greater than a length of the cannula in the compressed configuration.

4. The surgical access device of claim 1, further comprising a biasing element coupled to the cannula and configured to apply the biasing force to the cannula.

5. The surgical access device of claim 3, wherein the cannula has a maximum outer diameter in the compressed configuration that is greater than a maximum outer diameter of the cannula in the expanded configuration.

6. The surgical access device of claim 3, further comprising at least one seal element disposed within the working channel and configured to form at least one of a seal around an instrument disposed through the working channel and a seal across the working channel when no instrument is disposed therethrough.

7. A surgical access device, comprising;
a housing having a cannula extending distally therefrom, the housing and the cannula defining a working channel extending therethrough for receiving an instrument, the cannula being movable between an expanded configuration and a compressed configuration, and the cannula including a plurality of segments with a fluid-tight seal formed between adjacent ones of the segments such that the working channel is fluid tight when the cannula is in the expanded configuration and when the cannula is in the compressed configuration, wherein a biasing force biases the cannula to the compressed configuration; and
an adjustment mechanism coupled to the housing and configured to adjust the biasing force;
wherein the adjustment mechanism is selectively rotatable relative to the housing to adjust the biasing force.

8. The surgical access device of claim 7, wherein the cannula includes a distal-most anchor, and wherein rotation of the adjustment mechanism is effective to expand the distal-most anchor.

9. The surgical access device of claim 7, wherein the plurality of segments are removably coupled to one another.

10. A surgical access device, comprising:
a housing having a cannula extending distally therefrom, the housing and the cannula defining a working channel extending therethrough for receiving an instrument,; and
a plurality of biasing elements coupled to the cannula and configured to apply a biasing force to the cannula to bias the cannula to a compressed configuration, wherein less than a total number of the biasing elements are configured to be manipulated at a time to cause the cannula to bend and to cause adjustment of the biasing force.

11. The surgical access device of claim 10, wherein the plurality of biasing elements comprises a plurality of cables extending through the cannula.

12. The surgical access device of claim 11, wherein adjusting a length of at least one of the plurality of cables adjusts the biasing force.

13. The surgical access device of claim 10, wherein the cannula is movable between the compressed configuration and an expanded configuration, the cannula having a length in the expanded configuration that is greater than a length of the cannula in the compressed configuration.

14. The surgical access device of claim 13, wherein at least one of the biasing elements in configured to be manipulated to adjust the length of the cannula.

15. The surgical access device of claim 10, wherein the cannula is movable between the compressed configuration and an expanded configuration, the cannula having a maximum outer diameter in the compressed configuration that is greater than a maximum outer diameter of the cannula in the expanded configuration.

16. The surgical access device of claim 10, wherein the cannula includes a distal-most expandable anchor.

17. The surgical access device of claim 16, wherein the distal-most expandable anchor moves from an insertion configuration to an expanded configuration when the cannula is moved from an expanded configuration to the compressed configuration.

18. The surgical access device of claim 10, wherein the cannula comprises a plurality of segments movably coupled to one another.

19. The surgical access device of claim 10, further comprising at least one seal element disposed within the working channel and configured to form at least one of a seal around an instrument disposed through the working channel and a seal across the working channel when no instrument is disposed therethrough.

* * * * *